(12) United States Patent
Choonara et al.

(10) Patent No.: US 11,197,948 B2
(45) Date of Patent: Dec. 14, 2021

(54) THERMORESPONSIVE HYDROGEL

(71) Applicant: University of the Witwatersrand, Johannesburg, Johannesburg (ZA)

(72) Inventors: Yahya Essop Choonara, Johannesburg (ZA); Pierre Pavan Demarco Kondiah, Johannesburg (ZA); Pariksha Jolene Kondiah, Johannesburg (ZA); Pradeep Kumar, Johannesburg (ZA); Lisa Claire Du Toit, Johannesburg (ZA); Thashree Marimuthu, Johannesburg (ZA); Viness Pillay, Johannesburg (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 310 days.

(21) Appl. No.: 16/482,166

(22) PCT Filed: Jan. 31, 2018

(86) PCT No.: PCT/IB2018/050601
§ 371 (c)(1),
(2) Date: Jul. 30, 2019

(87) PCT Pub. No.: WO2018/142299
PCT Pub. Date: Aug. 9, 2018

(65) Prior Publication Data
US 2020/0054791 A1 Feb. 20, 2020

(30) Foreign Application Priority Data

Jan. 31, 2017 (ZA) .................. 2017/00391

(51) Int. Cl.
| | | |
|---|---|---|
| *A61L 27/52* | (2006.01) |
| *A61L 27/16* | (2006.01) |
| *A61L 27/18* | (2006.01) |
| *A61L 27/26* | (2006.01) |
| *B01J 31/12* | (2006.01) |
| *C08L 67/02* | (2006.01) |
| *C08L 67/04* | (2006.01) |
| *C08J 3/075* | (2006.01) |
| *A61L 27/50* | (2006.01) |
| *C08G 63/08* | (2006.01) |
| *C08L 67/06* | (2006.01) |

(52) U.S. Cl.
CPC ............... *A61L 27/52* (2013.01); *A61L 27/16* (2013.01); *A61L 27/18* (2013.01); *A61L 27/26* (2013.01); *B01J 31/12* (2013.01); *C08L 67/02* (2013.01); *C08L 67/04* (2013.01); *A61L 2400/06* (2013.01); *A61L 2430/02* (2013.01)

(58) Field of Classification Search
CPC .......... C08L 71/02; C08L 67/04; C08L 67/06; C08L 67/025; C08L 67/02; A61L 27/18; A61L 27/26; A61L 27/52; A61L 2400/06; A61L 2430/02; A61L 27/16; A61L 27/50; B01J 31/12; C08G 63/08; C08J 2367/06; C08J 3/075
See application file for complete search history.

(56) References Cited

U.S. PATENT DOCUMENTS

2008/0125870 A1   5/2008   Carmichael et al.

FOREIGN PATENT DOCUMENTS

WO   WO 2006/055940   5/2006

OTHER PUBLICATIONS

International Search Report for International Application No. PCT/IB2018/050601 dated May 24, 2018, 2 pages.
Written Opinion of the International Searching Authority for International Application No. PCT/IB2018/050601 dated May 24, 2018, 5 pages.

*Primary Examiner* — Jeffrey T. Palenik
(74) *Attorney, Agent, or Firm* — McDonnell Boehnen Hulbert & Berghoff LLP

(57) ABSTRACT

This invention relates to thermoresponsive hydrogels. Particularly, the invention relates to a thermoresponsive hydrogel comprising copolymer polyethylene glycol (PEG)-polycaprolactone (PCL)-polyethylene glycol (PEG) and polypropylene fumerate (PPF). The thermoresponsive hydrogel may further comprise a poloxamer, particularly Pluronic F-127. The invention extends to a method of manufacturing thermoresponsive hydrogels, also extends to an ink for a three dimensional (3D) printer including the thermoresponsive hydrogels. The invention further extends to a thermoresponsive hydrogel for use in the treatment of a bone injury and/or a bone defect, and/or to a method of treating a bone injury and/or a bone defect. The thermoresponsive hydrogels may include dispersed therein an active pharmaceutical ingredient (API), preferably an API falling in the Biopharmaceutics Classification System (BCS) class II, further preferably a statin type drug, most preferably simvastatin.

12 Claims, 17 Drawing Sheets a) Top view of the 3D bioprinted scaffold b) Isometric view of the 3D bioprinted scaffold c) Side view of the 3D bioprinted scaffold

THERMORESPONSIVE HYDROGEL

CROSS-REFERENCE TO RELATED APPLICATIONS

This application is a U.S. national phase application of International Patent Application no. PCT/IB2018/050601, filed Jan. 31, 2018, which claims the benefit of and priority to South African Application no. 2017/00391, filed Jan. 31, 2017, the contents of these applications being incorporated entirely herein by reference.

FIELD OF THE INVENTION

This invention relates to thermoresponsive hydrogels. Particularly, the invention relates to a thermoresponsive hydrogel comprising copolymer polyethylene glycol (PEG)-polycaprolactone (PCL)-polyethylene glycol (PEG) and polypropylene fumarate (PPF). The thermoresponsive hydrogel may further comprise a poloxamer, particularly Pluronic® F-127, also known as poloxamer 407. The invention extends to a method of manufacturing thermoresponsive hydrogels. The invention extends to a thermoresponsive hydrogel for use in the treatment of a bone injury and/or a bone defect, and/or to a method of treating a bone injury and/or a bone defect. The invention further extends to an ink for a three dimensional (3D) printer including the thermoresponsive hydrogels.

BACKGROUND TO THE INVENTION

Injury, age related bone defects, and as pathological conditions are some of the most common impairments related to bone and/or bone fractures. This usually results in a prolonged healing time, and in some instances, relapse occurs due to the treatment not reaching the specific site of action [1]. Current forms of treatment for these defects usually include bone grafts or metallic prosthetic implants. Allografts, xenografts, and autografts are categorized based on their natural tissue source. The most common form of bone implantation therapy is autografts, sampled from the patient's own body, thereby reducing the risk of tissue rejection. However, this form of therapy is restricted in many cases due to donor site morbidity, long recovery times, as well as substantial tissue damage resulting from surgery [2,3]. Consequently, principles of developing autografts and allograft bone substitutes, using biomaterial of a degradable and biocompatible nature, are increasing owing to the varying biological, structural and physico-mechanical properties that this engineering provides [4]. Research published in 2011 estimates over one million surgical procedures done involving bone defects in the United States (US) per year. This is as a result of trauma, along with non-union healing fractures requiring the implementation of bone grafts. This also affects older patients, thereby incurring greater strain on the healthcare industry, totaling greater than 5 billion dollars annually [5,6]. Hence, a significant alternative in the treatment of bone injuries is most certainly required, filling in the gaps of bone grafts, which cannot be undertaken in many instances, due to the limitations of current therapeutic procedures. This form of tissue engineering is a multifaceted specialization, involving chemical, biological and material science.

Many approaches exist for the development of an ideal bone engineered material, capable of increasing healing, adding support, and being biocompatible. It is essential to understand the limitations of this delivery while formulating a system that has exceptional physical, chemical, structural as well as biological composition, with a unique stimuli responsive system, enabled to deliver its loaded content most effectively.

There is a need to provide a material that mimics naturally occurring bone tissue for use in ameliorating at least one of the problems known to the field of bone injury and/or bone defects.

SUMMARY

In accordance with a first aspect of this invention there is provided a thermoresponsive hydrogel comprising a polyethylene glycol-polycaprolactone-polyethylene glycol (PEG-PCL-PEG) copolymer, polypropylene fumarate (PPF); and a poloxamer (POL).

The PEG-PCL-PEG: PPF:POL thermoresponsive hydrogel may be reversibly thermoresponsive across a temperature range, wherein an increase in temperature toward about human body (physiological) temperature increases a state of semi-solidity and/or solidity (by a decrease in viscosity) of the thermoresponsive hydrogel, and wherein a decrease in temperature away from about human body (physiological) temperature increases a state of liquidity (by an increase in viscosity) of the thermoresponsive hydrogel. An increase in temperature provides an increase in solidity, and a decrease in temperature provides an increase in liquidity.

The PEG-PCL-PEG:PPF:POL thermoresponsive hydrogel may be reversibly thermoresponsive across a temperature range transitioning from a sol (liquid) state, at about 20° C. or below about 20° C., to a gel (semi-solid) state, at about human body (physiological) temperature (about 36.5° C.) or above human body temperature (36.5° C.).

The temperature range may be from about 10° C., wherein the thermoresponsive hydrogel is in sol (liquid) state, to about human body temperature (about 36.5° C.), wherein the thermoresponsive hydrogel is in a gel (semi-solid) state. The gel (semi-solid) state may be a solid state.

The poloxamer may be Pluronic® F-127 (PF127), therein providing a PEG-PCL-PEG:PPF:PLF127 thermoresponsive hydrogel.

The thermoresponsive hydrogel may further comprise an active pharmaceutical ingredient (API) dispersed therein.

The active pharmaceutical ingredient (API) may be an API falling in the Biopharmaceutics Classification System (BCS) class II. The API of BCS class II may include for example, but not limited to, statins. Statins may include, for example, but not limited to, simvastatin and/or rosuvastatin.

When in use, the thermoresponsive hydrogel may be injected in sol (liquid) state at a site of bone injury and/or bone defect in a human or animal body, said thermoresponsive hydrogel may transition upon increasing in temperature closer to about human body (physiological) temperature (about 36.5° C.) to a gel (semi-solid) or solid state. When the thermoresponsive hydrogel is in a gel (semi-solid) or solid state and includes API, the thermoresponsive hydrogel provides for sustained and/or controlled release of said API at the site.

The sustained and/or controlled release may be over a number of days, preferably more than four days, further preferably more than eight day, still further preferably more than thirteen days.

The Applicant was surprised that from about 10° C. to about human (physiological) temperature (about 36.5° C.) the thermoresponsive hydrogel increased in strength by about 45 000 fold. The Applicant was further surprised that the physical morphology of the thermoresponsive hydrogel resembled mammalian, particularly human, bone tissue, therein being biomimetic in nature, and provides for sustained and/or controlled release of API (when at or about human physiological temperature) for up to and including fourteen days.

In accordance with a second aspect of this invention there is provided a method of manufacturing the thermoresponsive hydrogel according to the first aspect of the invention above, the method comprising the following steps:

(i). mixing ε-caprolactone (CL) and polyethylene glycol (PEG) together under inert conditions in the presence of a catalyst to form, via free radical polymerization, a first reaction mixture including a polyethylene glycol-polycaprolactone-polyethylene glycol (PEG-PCL-PEG) copolymer;

(ii). adding polypropylene fumarate (PPF) to the first reaction mixture forming a second reaction mixture; and (iii). mixing a poloxamer (POL) to the second reaction mixture to form a third reaction mixture including the thermoresponsive hydrogel according to claim 1.

The poloxamer may be Pluronic® F-127, also known as poloxamer 407. (PF127).

The catalyst may be stannous octoate $(Sn(Oct)_2)$.

The mixing of Step (i) may take place at about 125° C. for between 4 and 8 hours, preferably for 6 hours, and wherein the of Step (ii) may take place at about 140° C. for between 4 and 8 hours, preferably for 6 hours.

In accordance with a third aspect of this invention there is provided the thermoresponsive hydrogel according to the first aspect of the invention, for use in the treatment of bone injury and/or bone defects.

The thermoresponsive hydrogel may be for administration by injection in the sol (liquid) state at a site of bone injury and/or bone defect in a human or animal body, and wherein said injected thermoresponsive hydrogel transitions to a gel (semi-solid) state at said site.

The thermoresponsive hydrogel may be for administration by implantation in the semi-solid or solid state at a site of bone injury and/or bone defect in a human or animal body.

The solid or semi-solid thermoresponsive hydrogel for implantation may take on a peculiar shape and/or dimension. The peculiar shape and/or dimension may be three dimensionally printed utilizing a sol (liquid) form of the thermoresponsive hydrogel.

In accordance with a fourth aspect of this invention there is provided a method of treating a bone injury and/or a bone defect, the method comprising inserting the thermoresponsive hydrogel according to the first aspect of the invention at a site of bone injury and/or bone defect in a human or animal body.

The thermoresponsive hydrogel may be injected in the sol (liquid) state at the site of bone injury and/or bone defect, wherein said injected thermoresponsive hydrogel transitions to a gel (semi-solid) state at said site.

The thermoresponsive hydrogel may be in solid or semi-solid state, and may be implanted at the site of bone injury and/or bone defect.

The solid or semi-solid thermoresponsive hydrogel may take on a peculiar shape and/or dimension. The peculiar shape and/or dimension may be three dimensionally printed utilizing a sol (liquid) form of the thermoresponsive hydrogel.

In accordance with a fifth aspect of this invention there is provided an ink for a three dimensional printing device, the ink comprising the thermoresponsive hydrogel according to the first aspect of this invention.

There is further provided a thermoresponsive hydrogel, a method of manufacturing a thermoresponsive hydrogel, a thermoresponsive hydrogel for use in the treatment of a bone injury and/or a bone defect, a method of treating a bone injury and/or a bone defect and/or an ink for a three dimensional (3D) printer according to the first to fifth aspects of this invention, respectively, substantially as herein described, illustrated or exemplified with reference to any one of the accompanying diagrammatic drawings/figures and/or examples.

BRIEF DESCRIPTION OF THE DRAWINGS

Embodiments of the disclosure will be described below by way of example only and with reference to the accompanying drawings in which.

DETAILED DESCRIPTION OF PREFERRED EMBODIMENTS

Figure 1:
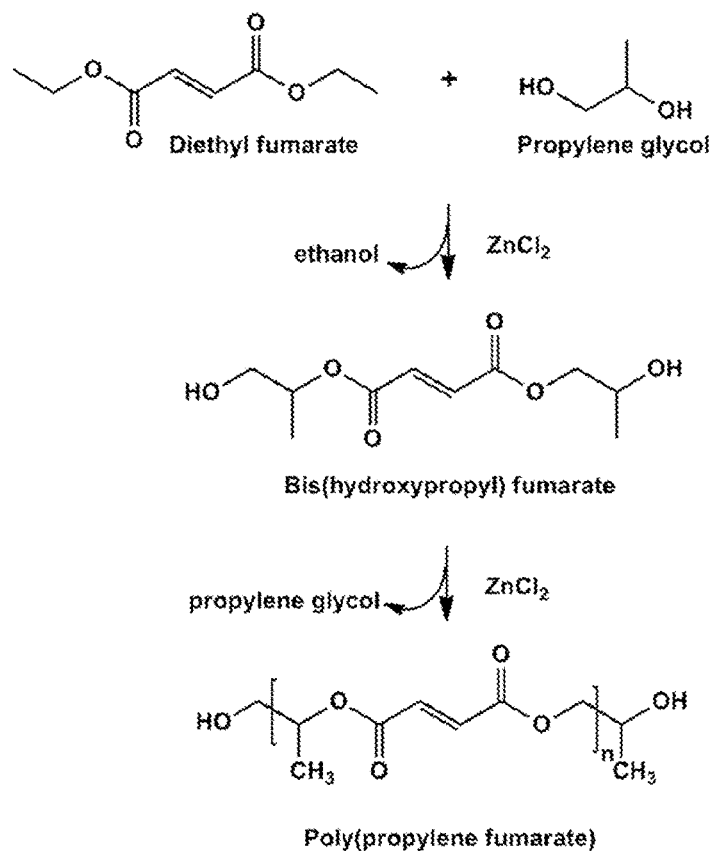
FIG. 1: shows a schematic representation of the synthesis for PPF, using a 2-step method involving bis(hydroxypropyl) fumarate as an intermediate.

The teachings of the Summary as repeated herein by reference thereto, and may not be fully repeated to avoid repetition.

In accordance with a first aspect of this invention there is provided a thermoresponsive hydrogel comprising a polyethylene glycol-polycaprolactone-polyethylene glycol (PEG-PCL-PEG) copolymer, polypropylene fumarate (PPF); and a poloxamer (POL). The poloxamer (POL) is typically Pluronic® F-127 (PF127) providing for a PEG-PCL-PEG:PPF:PF127 thermoresponsive hydrogel.

The PEG-PCL-PEG:PPF:PF127 thermoresponsive hydrogel is reversibly thermoresponsive across a temperature range, wherein an increase in temperature toward about human body (physiological) temperature increases a state of semi-solidity and/or solidity (by a decrease in viscosity) of the thermoresponsive hydrogel, and wherein a decrease in temperature away from about human body (physiological) temperature increases a state of liquidity (by an increase in viscosity) of the thermoresponsive hydrogel.

An increase in temperature provides a decrease in viscosity i.e. less able to flow and having greater solid state characteristics. A decrease in temperature provides an increase in viscosity i.e. more able to flow and having greater liquid state characteristics.

The PEG-PCL-PEG:PPF:PF127 thermoresponsive hydrogel is reversibly thermoresponsive across a temperature range transitioning from a sol (liquid) state, at about 10° C., to a gel (semi-solid) state or solid state, at about human body (physiological) temperature (about 36.5° C.). The gel (semi-solid) state may be a solid state.

Typically, the thermoresponsive hydrogel further comprises an active pharmaceutical ingredient (API) dispersed therein. The active pharmaceutical ingredient (API) is an API falling in the Biopharmaceutics Classification System (BCS) class II. The API of BCS class II is typically a statin. Statins include simvastatin and/or rosuvastatin.

When in use, the thermoresponsive hydrogel may be injected in sol (liquid) state at a site of bone injury and/or bone defect in a human or animal body, said thermoresponsive hydrogel transitions upon increasing in temperature closer to about human body (physiological) temperature (about 36.5° C.) to a gel (semi-solid) or solid state. When the thermoresponsive hydrogel is in a gel (semi-solid) or solid state and includes API, the thermoresponsive hydrogel provides for sustained and/or controlled release of said API at the site.

The sustained and/or controlled release may be over a number of days, preferably more than four days, further preferably more than eight day, still further preferably more than thirteen days.

The Applicant was surprised that from about 10° C. to about human (physiological) temperature (about 36.5° C.) the thermoresponsive hydrogel increased in strength by about 45 000 fold. The Applicant was further surprised that that physical morphology of the thermoresponsive hydrogel resembled mammalian, particularly human, bone tissue, therein being biomimetic in nature, and provides for sustained and/or controlled release of API (when at or about human physiological temperature) for up to and including fourteen days. The Applicant could not have predicted nor anticipated these unique properties upon an analysis of the component chemical compounds and/or component polymers of the thermoresponsive hydrogel.

The drastic increase in strength provides for a practical and/or effective biomimetic material that mimics bone tissue. Particularly, the thermoresponsive hydrogel provides a surface having similar physical features to that of bone tissue therein providing a platform for bone healing and/or repair via physiological and/or biochemical processes. The Applicant was surprised that the surface mimics bone tissue surface as seen in the SEM and TEM imaging experiments further herein below. This bio-mimicking decreases risk of rejection by the human or animal body. The strength ensures a prolonged lifespan of the thermoresponsive hydrogel when inserted into the human or animal body, and decreases the likelihood of repeated surgical procedures.

The Applicant believes the invention provides an effective and innovative solution to providing a biomimetic material that mimics bone tissue, is versatile in being injectable and implantable, and easy to use. The invention ameliorates at least one shortcoming of the prior art.

In accordance with a second aspect of this invention there is provided a method of manufacturing the thermoresponsive hydrogel according to the first aspect of the invention above, the method comprising the following steps:
(i). mixing ε-caprolactone (CL) and polyethylene glycol (PEG) together under inert conditions in the presence of a catalyst to form, via free radical polymerization, a first reaction mixture including a polyethylene glycol-polycaprolactone-polyethylene glycol (PEG-PCL-PEG) copolymer;

(ii). adding polypropylene fumarate (PPF) to the first reaction mixture forming a second reaction mixture; and (iii). mixing a poloxamer (POL) to the second reaction mixture to form a third reaction mixture including the thermoresponsive hydrogel according to claim 1.

The poloxamer may be Pluronic® F-127 (PF127).

The catalyst may be stannous octoate (Sn(Oct)$_2$).

The mixing of Step (i) may take place at about 125° C. for between 4 and 8 hours, preferably for 6 hours, and wherein Step (ii) may take place at about 140° C. for between 4 and 8 hours, preferably for 6 hours.

In accordance with a third aspect of this invention there is provided the thermoresponsive hydrogel according to the first aspect of the invention, for use in the treatment of bone injury and/or bone defects.

The thermoresponsive hydrogel may be for administration by injection in the sol (liquid) state at a site of bone injury and/or bone defect in a human or animal body, and wherein said injected thermoresponsive hydrogel transitions to a gel (semi-solid) state at said site.

The thermoresponsive hydrogel may be for administration by implantation in the semi-solid or solid state at a site of bone injury and/or bone defect in a human or animal body.

The solid or semi-solid thermoresponsive hydrogel for implantation may take on a peculiar shape and/or dimension. The peculiar shape and/or dimension may be three dimensionally printed utilizing a sol (liquid) form of the thermoresponsive hydrogel.

In accordance with a fourth aspect of this invention there is provided a method of treating a bone injury and/or a bone defect, the method comprising inserting the thermoresponsive hydrogel according to the first aspect of the invention at a site of bone injury and/or bone defect in a human or animal body.

The thermoresponsive hydrogel may be injected in the sol (liquid) state at the site of bone injury and/or bone defect, wherein said injected thermoresponsive hydrogel transitions to a gel (semi-solid) state at said site.

The thermoresponsive hydrogel may be in solid or semi-solid state, and may be implanted at the site of bone injury and/or bone defect.

The solid or semi-solid thermoresponsive hydrogel may take on a peculiar shape and/or dimension. The peculiar shape and/or dimension may be three dimensionally printed utilizing a sol (liquid) form of the thermoresponsive hydrogel.

In accordance with a fifth aspect of this invention there is provided an ink for a three dimensional printing device, the ink comprising the thermoresponsive hydrogel according to the first aspect of this invention.

The invention described herein at least ameliorates the disadvantages known in the prior art and/or described above. While the invention has been described in detail with respect to specific embodiments and/or examples thereof, it will be appreciated that those skilled in the art, upon attaining an understanding of the foregoing may readily conceive of alterations to, variations of and equivalents to these embodiments. Accordingly, the scope of the present invention should be assessed as that of the appended claims and any equivalents thereto.

EXAMPLES

Example 1

Experimental:

Synthesis of a PEG-PCL-PEG:PPF:PF127 Thermoresponsive Hydrogel in Accordance with this Invention:

In accordance with a first aspect of this invention there is provided a thermoresponsive hydrogel comprising polyethylene glycol (PEG)-polycaprolactone (PCL)-polyethylene glycol (PEG) and polypropylene fumarate (PPF). The thermoresponsive hydrogel typically further comprises a poloxamer, particularly Pluronic® F-127 to form a PEG-PCL-PEG:PPF:PF127 thermoresponsive hydrogel. The PEG-PCL-PEG:PPF:PF127 thermoresponsive hydrogel may be referred to as a copolymer blend of PPF, PEG-PCL-PEG and PF127. The thermoresponsive hydrogel may include dispersed therein an active pharmaceutical ingredient (API) or drug, preferably an API falling in the Biopharmaceutics Classification System (BCS) class II, further preferably a statin type drug, most preferably simvastatin (as exemplified herein). Below the second aspect of this invention, a method of manufacturing thermoresponsive hydrogels is described and exemplified.

Materials and Methods

Materials

Diethyl fumarate, 98%; diethyl ether (anhydrous); hydrochloric acid, 1.85% $^v/_v$; hydroquinone, 99% purity; methylene chloride; propylene glycol (1,2-propandiol); sodium sulphate and zinc chloride were purchased from Merck (Pty) Ltd. PEG (Mw 4000), epsilon (ε)-caprolactone, 99%; stannous octoate, 92.5%; petroleum ether, 90%; Pluronic® F-127; poly(ethylene glycol) diacrylate and simvastatin (molecular weight: 418.57), 97% purity, were procured from Sigma-Aldrich (St. Louis, Mo., USA).

All other reagents were of analytical grade and were employed as received. All synthetic reactions were carried out under inert conditions.

Synthesis of Poly (Propylene Fumarate) (PPF)

Poly (propylene fumarate) (PPF) was prepared by a two-step procedure involving bis(hydroxypropyl) fumarate as an intermediate owing to the relative lower by-product formation associated with this synthetic procedure, as seen in FIG. 1. Initially diethyl fumarate (30.52 g, 180 mmol) and propylene glycol (40.75 g, 540 mmol) were reacted in an oven-dried 500 mL round bottom flask (RBF), under inert conditions, at a temperature of 90° C. To this stirred solution, the crosslinking inhibitor hydroquinone (0.0303 g, 0.266 mmol), and the Lewis acid catalyst ZnCl$_2$ (0.2 g, 1.53 mmol) was added. Thereafter, the temperature of the system was increased to 110° C. Following this step, the temperature was gradually increased from 110° C. in increments of 10° C. every 30 minutes to 130° C. This reaction step yielded the intermediate bis(hydroxypropyl) fumarate and ethanol (distillate), and the reaction was ceased when 90% of the theoretical ethanol was collected in the receiving flask.

In the second step, the bis(hydroxypropyl) fumarate was transesterified to afford PPF and ethanol as the primary by-product. This reaction was carried out under vacuum (<1 mmHg) while the temperature was slowly increased from 100 to 130° C. (increment of 10° C. every 30) until the required molecular weight of PPF was obtained. The crude polymer product was thereafter dissolved in dichloromethane (DCM) and the reaction mixture was washed twice with a 1.85% $^v/_v$ solution of HCl to remove the catalyst. Thereafter the purification step was repeated with doubled-distilled water and portions of brine solution respectively. The organic phase was dried over anhydrous sodium sulphate, filtered and DCM was removed by rotary evaporation. The resulting polymer solution was poured into a previously chilled diethyl ether solution for removal off excess hydroquinone by precipitation of the purified PPF. Subsequently, the precipitate was isolated and re-suspended in DCM which was also removed under vacuum to yield the pure PPF polymer (Shung et al., 2002; Kasper et al., 2009., Timmer et al., 2003., Shulin et al., 2000).

Figure 2:
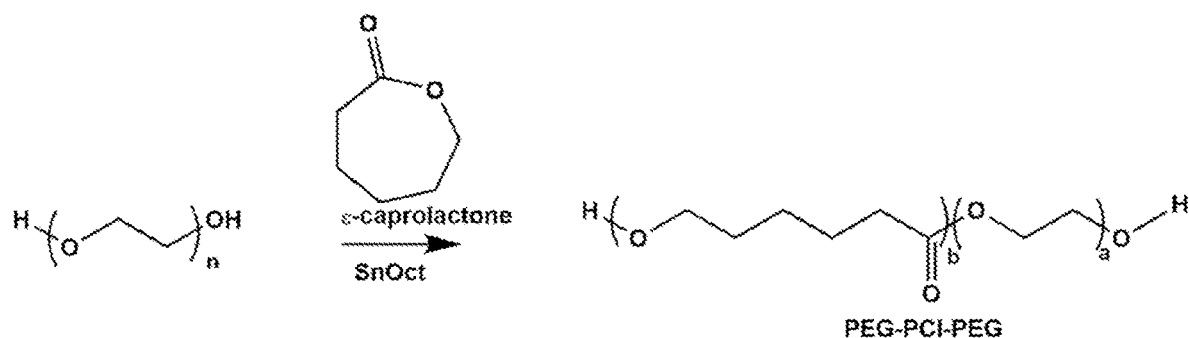
FIG. 2: shows a schematic representation strategy undertaken for the preparation of the PEG-PCL-PEG copolymer.

Preparation of PEG-PCL-PEG by Free Radical Polymerization & Preparation of the PEG-PCL-PEG:PPF:PF127 Thermoresponsive Hydrogel According to the Invention The copolymer polyethylene glycol-polycaprolactone-polyethylene glycol (PEG-PCL-PEG) blend was synthesized by free radical polymerization of ε-caprolactone using PEG (Mw 4000) as the macro initiator and stannous octoate, $Sn(Oct)_2$ as a catalyst. An oven dried 3-neck round-bottomed flask (RBF) equipped with a stir bar was charged with 0.007M of PEG 4000 and 0.098M of ε-caprolactone, capped with a rubber septum and flushed with nitrogen for several minutes. To the flask was added $Sn(Oct)_2$ (100 μL). A reaction temperature of 125° C. was maintained for 6 hours under constant purge of nitrogen gas. See FIG. 2.

Subsequently, synthesised PPF was added to the PEG-PCL-PEG to formulate 4 reaction mixtures (F1-F4) in triplicate. F1 and F3 were blended as 8% $^w/_v$ PPF, and F2 and F4 as 20% $^w/_v$ PPF. 16% $^w/_v$ Pluronic® F-127 was then added in all formulations. The ratios of PEG-PCL-PEG:PPF: PF127 was carried out as 4:1:1. Thereafter, the reaction temperature was increased to 140° C. and was maintained for 6 hours. The PEG-PCL-PEG:PPF:PF127 thermoresponsive hydrogel may be referred to as a copolymer blend of PPF, PEG-PCL-PEG and PF127.

The reaction mixture was then allowed to cool to room temperature and the copolymer blend was dissolved in DCM and precipitated with chilled petroleum ether. The resulting precipitate was filtered under vacuum and dried at room temperature for 24 hours. The resulting copolymer blend was evaluated using NMR, FTIR-ATR and XRD, evaluating its chemical characteristics as well as its crystalline and amorphous phases. The NMR, FTIR-ATR and XRD studies were conducted using non-drug/API loaded samples.

Drug (or API) Loading of the PEG-PCL-PEG:PPF:PF127 Thermoresponsive Hydrogel According to the First Aspect of this Invention:

Distilled water was added to the PEG-PCL-PEG:PPF: PF127 thermoresponsive hydrogel, (PEG-PCL-PEG:PPF: PF127: water ratio; 6.5:3.5), for its application of drug loading and in vitro studies. Drug/API (active pharmaceutical ingredient) was loaded in the thermo-gel at a temperature of 10° C. for 6 hours. Thereafter, the loaded thermo-gel was incubated at 25° C. for 2 hours, to ensure maximum drug loading occurred during the gelling phase. As exemplified herein simvastatin is used as an example drug/API. All the drug/API release studies include simvastatin as the example drug/API. The Applicant envisages utilizing other drugs/API apart from simvastatin.

Chemical Evaluation of the PEG-PCL-PEG:PPF:PF127 Thermoresponsive Hydrogel According to the First Aspect of this Invention:

Fourier transform infrared (FTIR) spectra was performed on PEG 4000, PEG-PCL-PEG, PPF and the PEG-PCL-PEG: PPF:PF127 thermoresponsive hydrogel according to this invention (the thermoresponsive hydrogel according to this invention is also herein referred herein as the "pseudo-bone thermo-gel").

FTIR spectroscopy (PerkinElmer Spectrum 2000) was used to evaluate the vibrational changes in the chemical structures of these compounds by using a single-reflection diamond MIRTGS detector (PerkinElmer Spectrum 100, Llantrisant, Wales, UK). Samples were placed on a single bounce diamond crystal and analysed by universal ATR (attenuate total reflectance) polarization accessory for the FTIR spectrum series. This was done at a resolution of 4 $cm^{-1}$, with the spectrum ranging from 4000-6000 $cm^{-1}$, at a constant pressure of 120 psi (pounds per square inch).

The Bruker AVANCE II 500 MHz (Bruker Avance Biospin, Germany) instrument was used to evaluate the nuclear magnetic resonance (NMR) spectra of the monomer, polymers and the pseudo-bone thermo-gel. Chemical shifts were evaluated in deuterated chloroform ($DCl_3$) as the solvent for analysing the samples at a temperature of 25° C.

X-ray diffraction (XRD) of the monomer, polymers and pseudo-bone thermo-gel was investigated using a Rigaku MiniFlex 600 Benchtop X-ray Diffractometer (Rigaku Corporation, Tokyo, Japan). The Rigaku MiniFlex guidance software (version 1.2.0) was used to evaluate the samples and the Rigaku PDXL basis software was utilized for analysis and determination of the degree of crystallinity of the samples. Samples were scanned at 0-100°/min. An angle diffraction range of 3°-60° 2θ was used.

Determination of Thermal Characteristics of the Monomers, Polymers and the PEG-PCL-PEG:PPF:PF127 Thermoresponsive Hydrogel:

Thermal properties of PEG 4000, PEG-PCL-PEG, PPF, PF-127 and the pseudo-bone thermo-gel (the PEG-PCL-PEG:PPF:PF127 thermoresponsive hydrogel) were assessed using the Mettler Toledo DSC-1 $STAR^e$ system (Mettler Toledo, DSC1, $STAR^e$ System, Swchwerzenback, Switzerland). Samples of 10 mg were weighed and sealed in a 40 μL aluminium crucible pan, with a 0.2 mm puncture on the lid of the pan. Inert atmospheric conditions were maintained, with a flow rate of 50 mL/min of $N_2$ gas, for the entire duration of assessment. Samples were analysed from 0° C. to 200° C., at a temperature ramping of 10° C./min, determining the thermal properties of the monomers, polymers and the pseudo-bone thermo-gel.

Determination of Viscoelastic Properties of the PEG-PCL-PEG:PPF:PF127 Thermoresponsive Hydrogel (Pseudo-Bone Thermo-Gel):

The viscoelastic behaviour of the pseudo-bone thermo-gel (the PEG-PCL-PEG:PPF:PF127 thermoresponsive hydrogel) was evaluated using a Modular Advanced Rheometer (ThermoHaake MARS Modular Advanced Rheometer, Thermo Electron, Karlsruhe, Germany), which comprises of a C35/1° Ti sensor. Rheological measurements were evaluated from 10-40° C., using a cone and plate inertia of $1.721 \times 10^6$ kg·$m^2$. 0.5 mL of the sample was examined over a range of 0-1.0 Hz, falling within the shear independent plateau of the strain amplitude sweep stress (Nneji et al., 2015; Guangzhong et al., 2015; Gioffredi et al., 2016). The effects of elastic energy (storage modulus or G'), viscous energy (loss modulus or G") or a resultant of both can be observed after subjecting the sample to sinusoidal oscillation (Schramm et al., 2004).

Surface and Structural Morphological Evaluation of the PEG-PCL-PEG:PPF:PF127 Thermoresponsive Hydrogel (Pseudo-Bone Thermo-Gel):

The surface morphology of the pseudo-bone thermo-gel (the PEG-PCL-PEG:PPF:PF127 thermoresponsive hydrogel) was analysed using scanning electron microscopy (SEM). The sample was sputter coated on an aluminium spud, by an EPI sputter coater (SPI Module™ sputter-coater and control unit, West Chester, Pa., USA), using gold compound. The FEI ESEM Quanta 400F (FEI™, Hillsboro, Oreg., USA) electron microscope, using an electron acceleration charge of 20 kV, was used to produce high resolution images of the particles.

The structural morphology was carried out using transmission electron microscopy (TEM) (Jeol 1200 EX, Japan). The PEG-PCL-PEG:PPF:PF127 thermoresponsive hydrogel was suspended in double distilled water (0.5 mg/mL). A drop was placed on a 200 mesh thick formvar copper grid (TABB Laboratories Equipment, Berks, UK), using a pipette. The PEG-PCL-PEG:PPF:PF127 thermoresponsive hydrogel was left to be adsorbed onto the surface of the copper grid. A drop of 2% $^v/_w$ uranyl acetate in double distilled water was thereafter added to the adsorbed copolymeric system. This was left to dry at room temperature for an hour before evaluation.

In Vitro Drug Release of the PEG-PCL-PEG:PPF:PF127 Thermoresponsive Hydrogel (Pseudo-Bone Thermo-Gel):

Distilled water was added to the pseudo-bone thermo-gel (the PEG-PCL-PEG:PPF:PF127 thermoresponsive hydrogel), (PEG-PCL-PEG:PPF:PF127: water ratio; 6.5:3.5), for its application of drug loading and release analysis. 10 mg drug was loaded in the thermo-gel at a temperature of 10° C. for 6 hours. Thereafter, the loaded thermo-gel was incubated at 25° C. for 2 hours, to ensure maximum drug loading occurred during the gelling phase.

In vitro drug release was undertaken on 4 formulations, with a therapeutic dose of 10 mg simvastatin loaded in all formulations (n=3). The formulations were evaluated, using 8% $^w/_v$ and 20% $^w/_v$ concentrations of PPF, varying the temperature evaluation conditions at 25° C. and 37.5° C. F1 and F3 were blended as 8% $^w/_v$ PPF, and F2 and F4 as 20% $^w/_v$ PPF. F1 and F2 were evaluated at room temperature (25° C.) and F3 and F4 at body temperature (37.5° C.).

As seen in rheological evaluation, at room temperature (±25° C.), the sample begins to gel. Therefore, release of simvastatin at room temperature in comparison to body temperature was undertaken, evaluating the controlled mechanism of release at body temperature, in relation to normal room temperature behaviour.

In vitro drug release analysis was carried out employing dialysis membranes (MWCO: 1.2 kDa) in a buffer solution (PBS pH 6.8). An orbit shaker incubator (LM-530-2, MRC Laboratory Instruments Ltd, Hahistadrut, Holon, Israel) at 37±0.5° C., with 50 rpm, was used to incubate all samples during the entire duration of the release studies. 1 mL of sample was withdrawn at each time point for analysis and replaced with the same volume of fresh buffer. This was done to maintain sink physiological conditions throughout the entire duration of the release studies. For evaluation at room temperature, samples were magnetically stirred at 50 rpm, maintaining sink conditions as mentioned above. Samples were analysed using UV spectrophotometer, at wavelength 238 nm (IMPLEN Nanophotometer™, Implen GmbH, München Germany), using a 10 times dilution factor of path-length 0.1 mm (Bte et al., 2011; Zhang et al., 2011).

Inducing a Butterfly Bone Fracture and Evaluating Fractal Dimensions on Human Clavicle Bones:

The relationship between bone fractal properties are significantly dependant on macro and microscopic density, mass and volume of porous nature, with significant correlation to pore size properties. The state of bone in normal and osteoporotic bone is drastically different in its gross composition. Therefore, patients with this bone condition run the risk of various bone injuries and complications. It is for this situation of osteoporosis and bone related injuries that a pseudo-bone thermo-gel (the PEG-PCL-PEG:PPF:PF127 thermoresponsive hydrogel) was formulated and evaluated. In this instance, the physical dimensions of a human clavicle bone were investigated, determining its fractal magnitude.

The Applicant evaluated osteoporotic female human dried clavicle bones and induced 4 mm diameter fractures in the region between the cervical fascia and the area bellow the conoid tubercle (Sanchez-Molina et al., 2013). The clavicle bones were acquired from the Department of Anatomical Sciences, University of the Witwatersrand, South Africa with ethical waiver clearance. The bones were evaluated using X-ray and ultrasound imaging. Real-time ultrasound imaging of the human clavicle bones was visualized using a high-frequency ultrasound scanner (Vevo® 2100, Visualsonics, Toronto, Ontario, Canada) with an MS-250 transducer. The bones were evaluated with X-ray and ultrasound before and after inducing a 4 mm diameter butterfly-fracture.

The butterfly fracture was induced using a 4 mm punch and dye apparatus, using a hydraulic pressure of 0.6 MPa. The bones were evaluated with X-ray and ultrasound once again after injecting the bones at the site of fracture with the pseudo-bone thermo-gel, and incubating the bones for 15 min in an orbital shaker bath, immersed in phosphate buffer solution (PBS). A well calibrated textual analyzer (TA.XTplus, Stable Microsystems, Surrey, UK), under standard conditions (temperature of 25° C. and pressure of 1 atm), was used to evaluate the matrix hardness (MH) and matrix resilience (MR) on the bones before inducing the fracture and after treatment with the injected pseudo-bone thermo-gel on the fractured bones respectively. A steel flat tip probe of 2 mm diameter was used to determine MH and a steel cylindrical probe of 50 mm diameter for determination of MR.

Figure 3:
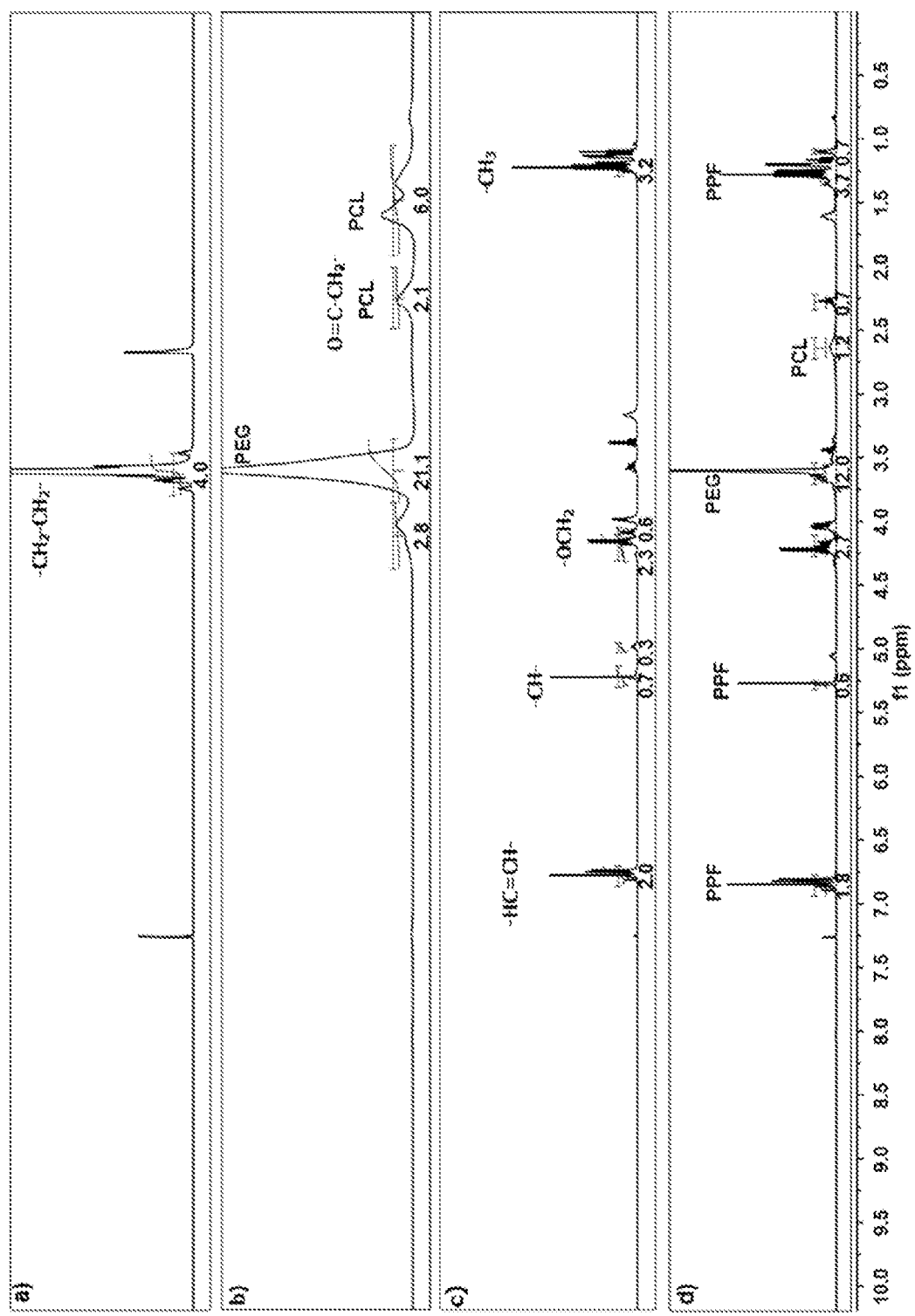
FIG. 3: shows an $H^1$ NMR evaluation for monomers, polymers and the pseudo-bone thermo-gel; a) $PEG_{4000}$, b) PEG-PCL-PEG, c) PPF and d) Pseudo-bone thermo-gel (also termed herein as the PEG-PCL-PEG:PPF:PF127 thermoresponsive hydrogel, according to the first aspect of the invention).

Results and Discussion (Example 1):

Chemical Evaluation Undertaken on Monomers, Polymers and the Pseudo-Bone Thermo-Gel (the PEG-PCL-PEG:PPF:PF127 Thermoresponsive Hydrogel):

$^1$HNMR evaluation, ATR-FTIR and XRD analysis was carried out on individual monomers, polymers, as well as the pseudo-bone thermo-gel (the PEG-PCL-PEG:PPF:PF127 thermoresponsive hydrogel). $PEG_{4000}$ (a), PEG-PCL-PEG (b), PPF (c) and the pseudo-bone thermo-gel (d) were evaluated for all the above mentioned chemical characteristic analysis. $^1$HNMR is seen in FIG. 3, with a peak commonly observed in all spectras at 7.25 ppm being deuterated chloroform as the selected solvent for analysis.

As seen in FIG. 3a, significant —$CH_2$— and —$CH_2CHO$— groups are displayed at 3.5 ppm and 3.65 ppm respectively. FIG. 3b displays characteristic functional groups of PEG-PCL-PEG, with peaks in the regions of 3.35, 1.6, 2.2 and 3.92 ppm attributed to methylene protons of —$(CH_2)_3$—, —$OCCH_2$—, and —$CH_2OOC$— in the PCL block unit. The peak reflected at 3.65 ppm in PEG-PCL-PEG can be clearly attributed to the PEG unit, signalling —$CH_2CHO$— functionalities. As reflected by the synthesis of this PEG-PCL-PEG:PPF:PF127 thermoresponsive hydrogel, it was further confirmed that the ratio of PEG:PCL was 3.5:1. This was significant due to the desire for a high capacity of hydrophilicity of the copolymer, with further implementation for its precursor synthesis reaction for the thermo-gel.

FIG. 3c reflects the successful synthesis of PPF. Major peaks are seen in the regions of 6.75, 5.29, 4.25, 4.24 and 1.2 ppm, designated to the olefinic (O=C—CH=CH—C=O), methine, methylene and methyl protons repated respectively. A range of minor peaks are also evident in the spectrum, ranging from 4.9, 4.22, 4.09, 3.7, 1.28 and 1.22 ppm. These groups are signified as the end groups of the PPF polymeric chain unit. Integrating these major and minor peaks, the average molecular weight ($M_n$) of PPF polymer was established as ~1000 Da, falling in the reported range of 500-4000 Da (Kasper et al., 2009).

FIG. 3d reflects the spectrum of the thermo-gel copolymer blend (the PEG-PCL-PEG:PPF:PF127 thermoresponsive hydrogel), with various shifts occurring in the backbone of PPF. In the regions of 3.5 and 3.65 ppm, broad signal —($CH_2$) PEG functionalities are retained, further accompaning peaks in the regions of 1.6 and 2.2 ppm, due to the PCL block unit present in the thermo-gel copolymer blend, with functional groups of —$OCCH_2$—, and —$CH_2OOC$— reflected respectively. In the region of 1.1 ppm, —$CH_3$— groups of PF127 are evident. In the region of 6.75 ppm, —HC═CH— of PPF was noticably unaffected due to the non-participation of these functionalities.

Further evaluation of the spectrum reflected no chemical shifts for —$CH_3$— protons in the backbone of PEG-PCL, however peaks observed in the region 1-1.3 ppm are most likely due to —$CH_3$— groups found in PPF and PF127, appearing as chemical shifts from the parent compounds respectively. PF127 peaks were also observed at 3.4 ppm, attributed to the hydrogen atoms of individual functional groups. Further elimination of the minor peaks of PPF in the thermo-gel suggests successful copolymeric blending in the thermo-gel, with the end groups of the PPF polymeric chain unit eliminated (Zhou et al., 2011; Behravesh et al., 2002; Jo et al., 2000).

Figure 4:
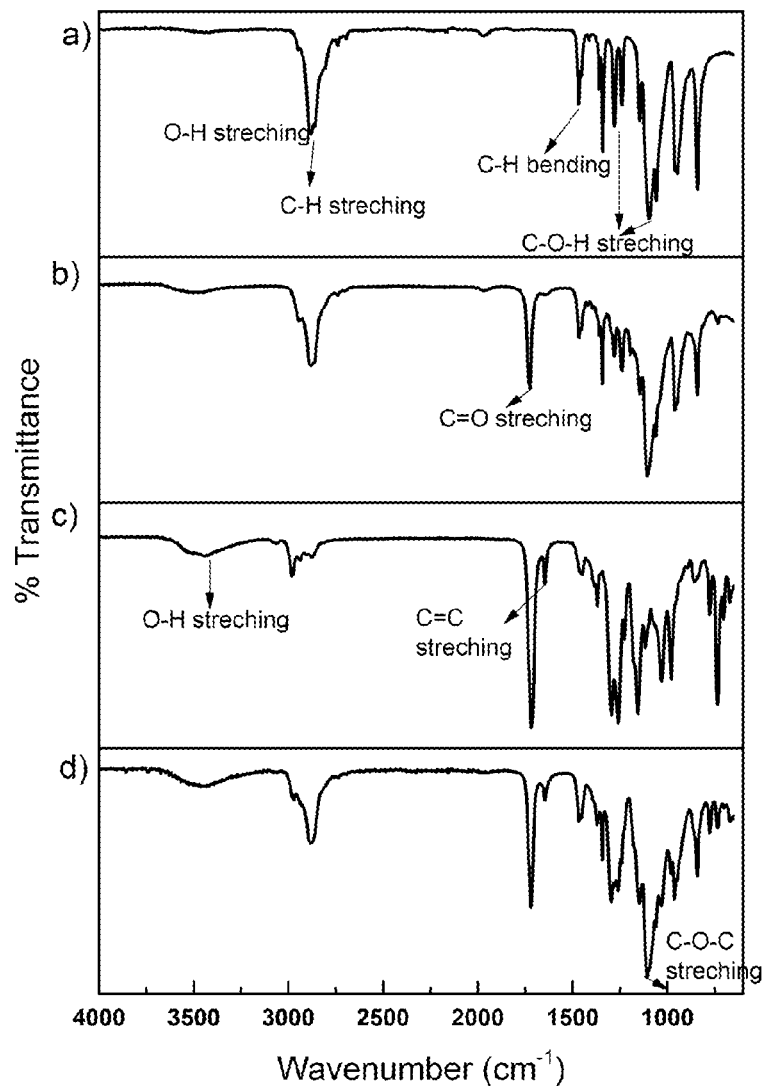
FIG. 4: shows an ATR-FTIR analysis undertaken on; a) $PEG_{4000}$, b) PEG-PCL-PEG c) PPF and d) Pseudo-bone thermo-gel.

ART-FTIR spectra analysis as seen in FIG. 4 further supports results obtained in $^1$HNMR analysis. As denoted in FIG. 4a for $PEG_{4000}$, significant functional groups are marked, showing —O—H—, —C—H— and —C—O—H— stretching in the regions of 2950 $cm^{-1}$, 2780 $cm^{-1}$, and 1350 $cm^{-1}$ respectively. In the copolymer of PEG-PCL-PEG (FIG. 4b), the characteristic peaks at 3500 $cm^{-1}$, 2900 $cm^{-1}$-2800 $cm^{-1}$, 1733 $cm^{-1}$ and 1152 $cm^{-1}$-1100 $cm^{-1}$, are signals of —OH, —$CH_2$, C═O, C—O—C, and —COO— bands respectively. For PPF (FIG. 4c), characteristic peaks at 1713 $cm^{-1}$, 1645 $cm^{-1}$, 1250 $cm^{-1}$ and 1149 $cm^{-1}$ are indicative of C═O stretching, C≡C stretching, asymmetric C—O—C stretching and symmetric C—O—C stretching bands respectively.

The peak observed at 1645 $cm^{-1}$ in PPF (FIG. 4c) and the pseudo-bone thermo-gel (FIG. 4d), further substantiates that the C═C double bond was not affected in the copolymeric chain unites, after blending occurred to form the thermo-gel. Further peaks in the regions 1570 $cm^{-1}$, 1378 $cm^{-1}$ and 1166 $cm^{-1}$ in the thermo-gel (FIG. 4d), are attributed to the asymmetric and symmetric $CO_2$— bands of stretching respectively, thereby further indicating successful formulation of the pseudo-bone thermo-gel. An overlap of strong C═O stretching in the region of 1730 $cm^{-1}$ was observed for PEG-PCL-PEG, PPF and PF127. These strong ester bonds can be seen in the thermo-gel due to the blending of PPF and PF127 with PEG-PCL-PEG copolymer.

The stretching vibrations of C—H of the PEO unit in PF127 are shifted slightly and evident in the thermo-gel (FIG. 4d) in the regions of 2975 $cm^{-1}$ and 2880 $cm^{-1}$. The intensity of the signal at 1118 $cm^{-1}$ is clearly indicative of C—O—C stretching vibration of PF127 in the thermo-gel. The resulting functional peaks thus implies successful blending of the polymers to form the pseudo-bone thermo-gel system (the PEG-PCL-PEG:PPF:PF127 thermoresponsive hydrogel).

Using XRD analysis, the pseudo-bone thermo-gel (the PEG-PCL-PEG:PPF:PF127 thermoresponsive hydrogel) displayed greater crystallinity than PPF and PEG-PCL-PEG. $PEG_{4000}$ (FIG. 5a) displayed distinctive sharp peaks at 2 theta=20.2° and 22.7° due to a high molecular weight of PEG used. In PEG-PCL-PEG (FIG. 5b), these peaks are no longer sharp and narrow due to the segments of the PEG-PCL-PEG copolymer becoming amorphous with the incorporation of PCL.

PEG-PCL-PEG copolymer also reflected peaks at 2 theta=21.6° and 23.5°, correlating to the lattice planes of orthorhombic PCL unites (Yin et al., 2015). As seen in PPF (FIG. 5c), a substantial amorphous arrangement of the polymer is reflected.

Figure 5:
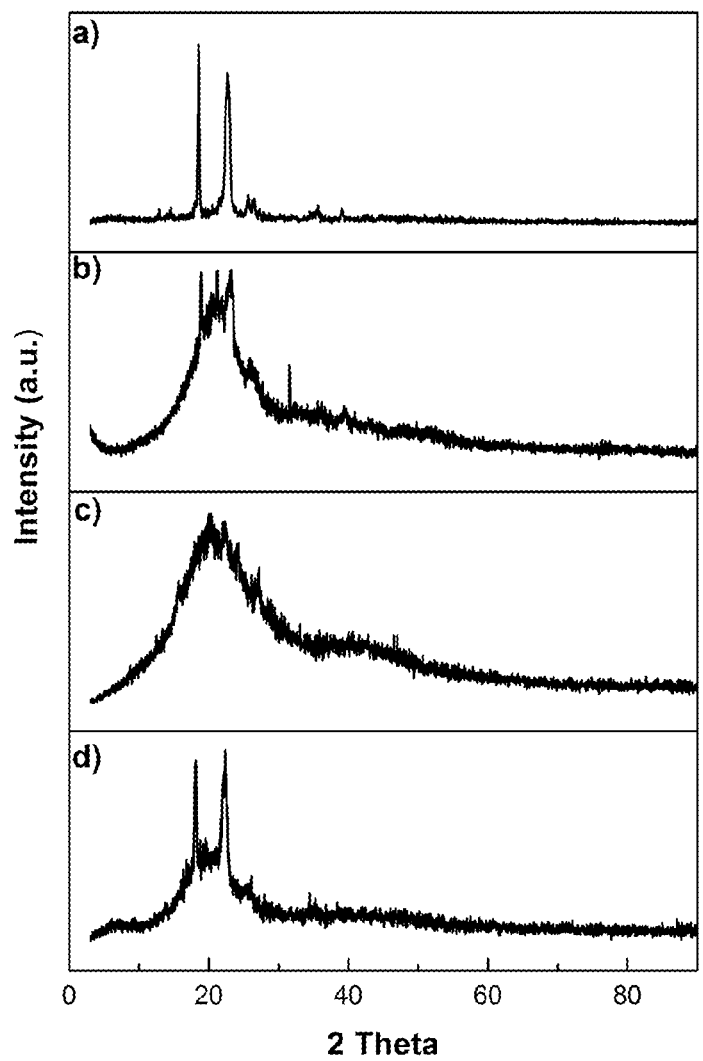
FIG. 5: shows an XRD analysis undertaken on a) $PEG_{4000}$, b) PEG-PCL-PEG c) PPF and d) Pseudo-bone thermo-gel.

FIG. 5d illustrates the thermo-gel (the PEG-PCL-PEG:PPF:PF127 thermoresponsive hydrogel), showing a semi-crystalline nature of the copolymer blend. This can be attributed to the high crystallinity of the PEG unit, further reflecting these peaks of PEG in the thermo-gel. The thermo-gel also demonstrated higher crystalline nature than PEG-PCL-PEG and PPF, further reasoning the advantage of blending these polymers to obtain a higher crystalline copolymer blend which is confirmed at 2 theta=19.4 and 23.9°.

This semi-crystalline nature also substantiates the slow-release in vitro kinetics of the pseudo-bone thermo-gel, which is discussed in detail in the later sections of the paper. This property allows a uniform sustained release of the loaded drug in the thermo-gel, thereby reacting to the thermal stimulus, releasing its loaded drug over a prolonged duration of time. The semi-crystalline nature of the pseudo-bone thermo-gel further enhances the amphiphilic drug release properties, promoting greater drug loading capacity due to a substantial hydrophobic affinity for the statin-loaded thermo-gel copolymer blend. It can therefore be confirmed that the thermo-gel has a greater order of molecules in its crystal lattice. This can be attributed to many factors such as chain lengths, inter-chain interactions and chain branching interactions (www.chemistry.msu.com).

Figure 6:
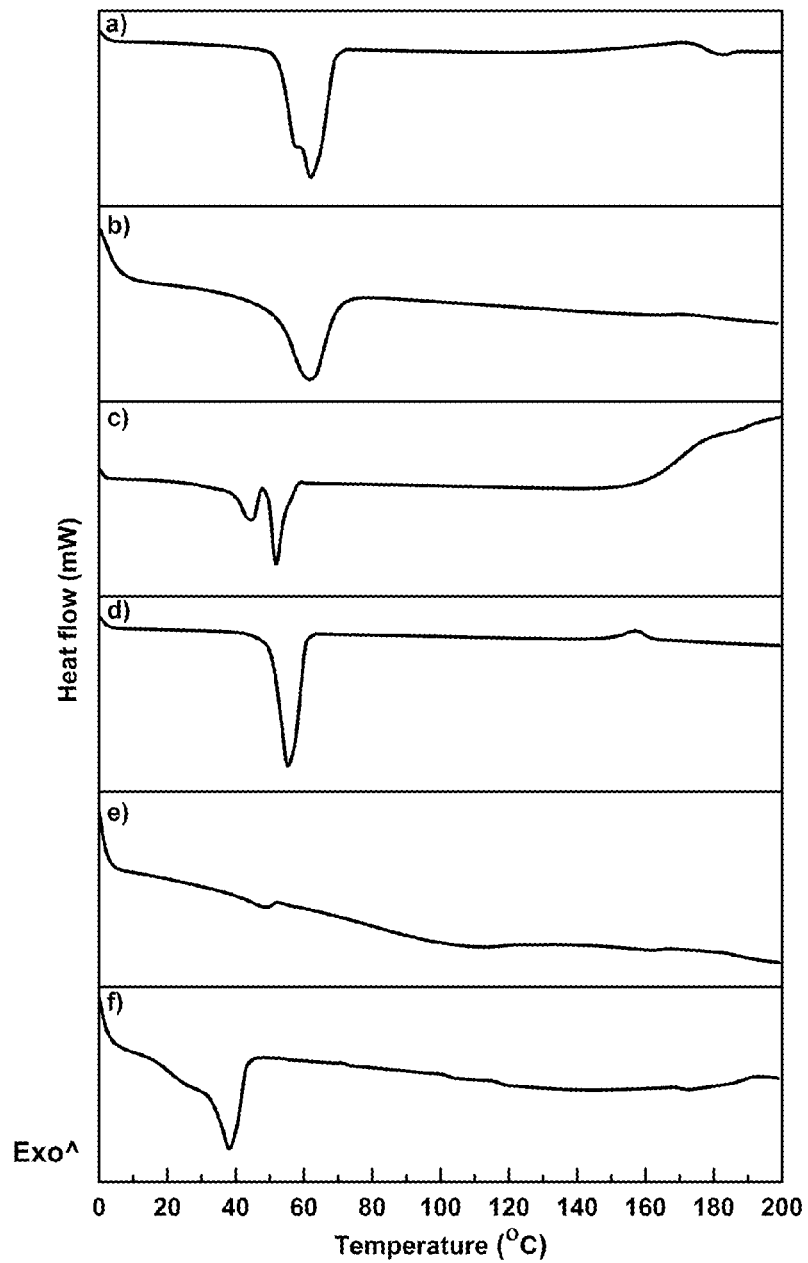
FIG. 6: shows a DSC undertaken on monomer, polymers and the pseudo-bone thermo-gel; a) $PEG_{4000}$, b) PEG-PCL-PEG c) PF127, d) PPF and e) Pseudo-bone thermo-gel.

Thermal Evaluation of the Monomers, Polymers and the Pseudo-Bone Thermo-Gel (the PEG-PCL-PEG:PPF:PF127 Thermoresponsive Hydrogel):

DSC was undertaken on $PEG_{4000}$, PCL, PEG-PCL-PEG, PF127, PPF and the pseudo-bone thermo-gel (the PEG-PCL-PEG:PPF:PF127 thermoresponsive hydrogel). The DSC thermogram of PEG-4000 exhibited two split melting endotherm peaks at 57.13° C. and 61.71° C. respectively (FIG. 6a). This observation is significantly due to the existence of both folded and extended chains in the PEG matrix (Ginés et al, 1996). The endotherm peak at 61.93° C. in the thermogram of PCL (FIG. 6b) was indicative of melting, and shifted to 51.90° C. in the thermogram of PEG-PCL-PEG (FIG. 6c). The endotherm at 44.48° C. in FIG. 6c can be attributed to melting of the PEG crystal domains through the heating period (Zhou et al., 2003). As seen in PF127 (FIG. 6d), the melting of crystalline phases was observed at 55.18° C. In FIG. 6e, it was observed that PPF displayed a slight transition in its amorphous polymer state in the region of 4.05° C. (Lee et al., 2006). The pseudo-bone thermo-gel (FIG. 6f) displayed a broad endotherm in the region of 20.7° C.-38.18° C., attributed to the aliphatic flexible chains coupled in PEG-PCL-PEG and PF127. Characteristic peaks of PPF could not be significantly observed in the thermogel, due to the diminishing free chain ends after copolymeric blending (Lee et al., 2006).

Figure 7:
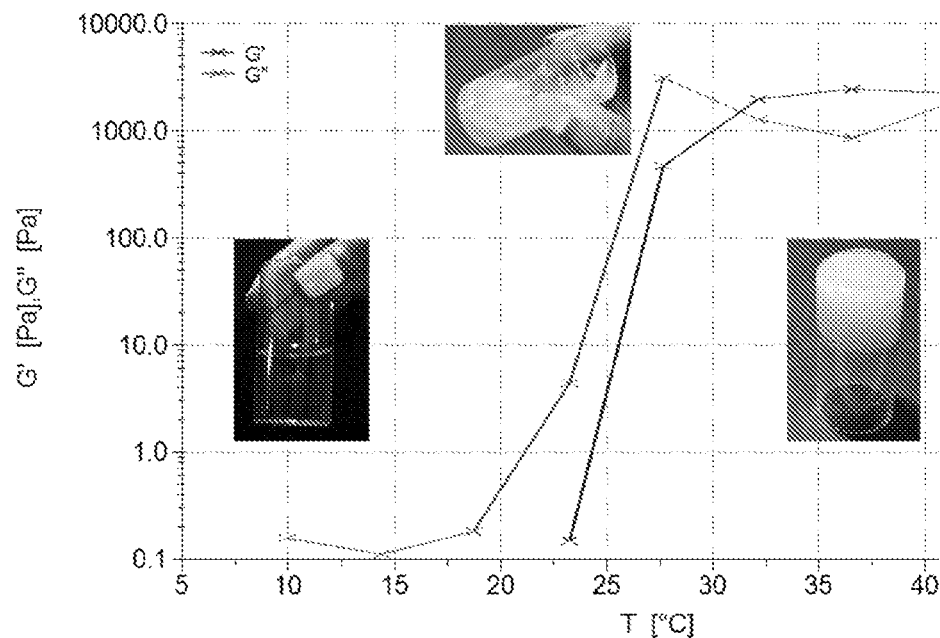
FIG. 7: shows a rheological evaluation of the pseudo-bone thermo-gel in relation to change in temperature.

Determination of Storage and Loss Modulus of the Pseudo-Bone Thermo-Gel (the PEG-PCL-PEG:PPF:PF127 Thermoresponsive Hydrogel):

The pseudo-bone thermo-gel (the PEG-PCL-PEG:PPF:PF127 thermoresponsive hydrogel) was evaluated with respect to change in temperature, at a constant applied force, evaluating the characteristic response of the thermo-gel due to change in temperature, as seen in FIG. 7. G' is described as the measure of deformation energy within the pseudo-bone thermo-gel, referring to the elastic, solid properties of the thermo-gel. In contrast, G" is the measure of the viscous and deformation energy used and lost in the thermo-gel over a given temperature range. As seen in FIG. 7, G' begins at 23° C., starting to form a semi-solid gelling property, and thereafter at 32° C., completely switches to the elastic phase property, remaining above G" throughout the evaluation of the sample. It was observed that the viscosity of the sample gradually increases above room temperature, ±25° C., maintaining a higher elastic phase property (gel) than the liquid state (sol) at body temperature conditions.

The thermo-gel will be injected at the site of the small bone fracture. At this stage, the body temperature will allow the thermo-gel to increase its visco-elastic properties, forming a semi-solid material at the site of bone injury. Since all materials employed in the copolymer blend are approved biodegradable and biocompatible, the gel will degrade and release its loaded drug over a prolonged duration of time, in a controlled release mechanism. The thermo-gel system at body temperature does not become brittle and cracked, instead as seen in the rheological evaluation, maintains a high elastic property, and acts like a 'glue-like' substance, filling the gaps between the fracture site and further allowing significant adhesion of the bone to promote substantial healing. The loaded drug in the pseudo-bone thermo-gel is further released and absorbed at the site of injury, promoting exponential repair of the bone in a shortened time period, behaving as a controlled release system (Zhang et al., 2009; Feng et al., 2014; Vandenhaute et al., 2014).

The Applicant therefore conclude that the pseudo-bone thermo-gel has substantial thermo-responsive properties, with a significant change in modulus due to temperature variations. At controlled storage temperature 10-20° C. (ideal and safe storage would be refrigeration at 10° C.), only viscous modulus is present in the range of 0.1-0.3 Pa. When physiological temperature is reached, the thermo-gel increases strength by 45 000 times (from 0.1 Pa to 4500 Pa). As body temperature is reached by the thermo-gel, the gel forms a solid, semi-elastic substance, thereby gradually releasing drug in a controlled, sustainable manner.

Predicting the thermoresponsive property, and in particular an increase in strength by 45 000 times was not suggested by analysis of the individual components of the PEG-PCL-PEG:PPF:PF127 thermoresponsive hydrogel.

Figure 8:
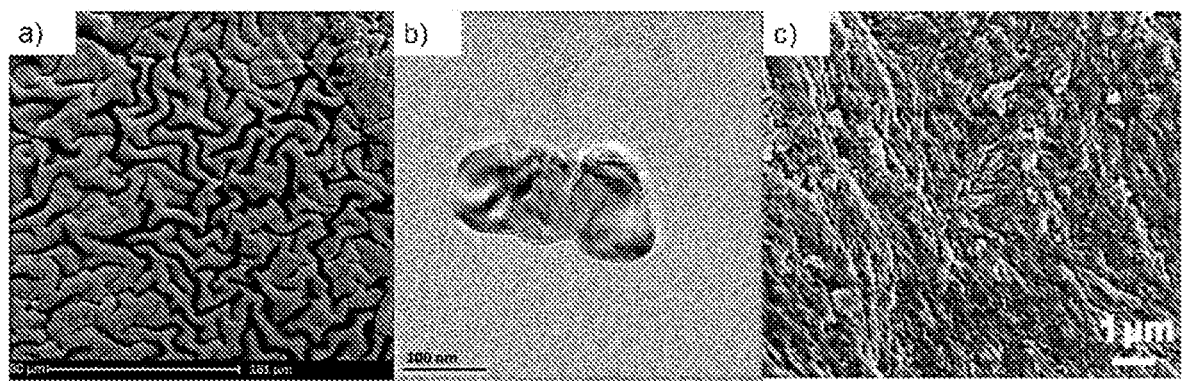
FIG. 8: shows a morphological evaluation undertaken, reflecting; a) SEM analysis on the pseudo-bone thermo-gel, b) TEM analysis on the pseudo-bone thermo-gel; and c) comparative SEM imaging of human bone under high magnification.

Surface and Structural Morphological Evaluation of the Pseudo-bone Thermo-Gel (the PEG-PCL-PEG:PPF:PF127 Thermoresponsive Hydrogel):

SEM and TEM analysis was undertaken on the pseudo-bone thermo-gel to determine the morphological properties of the thermo-gel system (the PEG-PCL-PEG:PPF:PF127 thermoresponsive hydrogel). As seen in FIG. 8a, SEM reflects the copolymer blend network of the thermo-gel, with distinctive intertwined patterns, forming a uniformed regular arrangement. This can be correlated to results obtained in XRD analysis, complementing the semi-crystalline nature of the pseudo-bone thermo-gel. The ordered arrangement of the pseudo-bone thermo-gel demonstrates substantial potential for high drug entrapment and release properties. Drug release properties from the pseudo-bone thermo-gel highly correlates with the structural arrangement of the micrograph, evidently due to the highly ordered arrangement of the particles in the pseudo-bone thermo-gel.

TEM analysis was then sought for viewing individual copolymeric blend particles as seen in FIG. 8b. Particles appeared ovoid in nature with an average diameter of 80 nm, further confirmed using particle size analysis. The TEM image can be viewed as 3 particles overlapped on one another (each particle on the side, with another particle in the centre of each), with a clear representation of the distinctive outline of each particle. Due to substantial dilutions of preparing the sample for evaluation, a final distinctive image was obtained viewing a single particle out of the highly inter-penetrating network of particles in the pseudo-bone thermo-gel system. Samples were evaluated at room temperature, making it easier to view a 'less clumped' state of particles with less water absorbed in this conformation (Gong et al., 2009; Rainer et al; 2012). The particle uniformity is essential for volume and surface area advantages, thereby having a greater capacity to predict the desirable behaviour of the pseudo-bone thermo-gel in vivo due to reliable kinetics based on the morphological characteristics of the uniform copolymer blend particles (Pandit et al., 1996; Volkmer et al., 2013; Niu et al., 2009). An SEM of bone tissue under high magnification was also compared to the pseudo-bone thermo-gel (FIG. 8c). As seen in these images, a comparable conformational network is observed in bone tissue and the pseudo-bone thermo-gel. This array of interpenetrating networks with various pores can be seen in bone tissue and the pseudo-bone thermo-gel. Due to these morphological similarities, the corresponding mechanical nature of the pseudo-bone thermo-gel can be understood. Using these blended copolymers, the resulting thermo-gel (the PEG-PCL-PEG:PPF:PF127 thermoresponsive hydrogel) not only resembles morphological similarities to bone, but also matrix hardness and resilience properties in situ, when exposed to physiological parameters, as discussed herein above. The thermo-responsive nature of the PEG-PCL-PEG:PPF:PF127 thermoresponsive hydrogel allows a defined tightly packed network of particles to resemble bone tissue surface conformation, evidently supporting its structure by a continuous alignment of interconnected copolymeric network particles.

The PEG-PCL-PEG:PPF:PF127 thermoresponsive hydrogel has substantial potential for application as an injectable delivery system, supported morphologically by SEM and TEM analysis. Predicting these properties when considering the component parts or component polymers was not possible. The Applicant was surprised that the thermoresponsive hydrogel according to the invention mimics bone tissue as illustrated above and herein.

Figure 9:
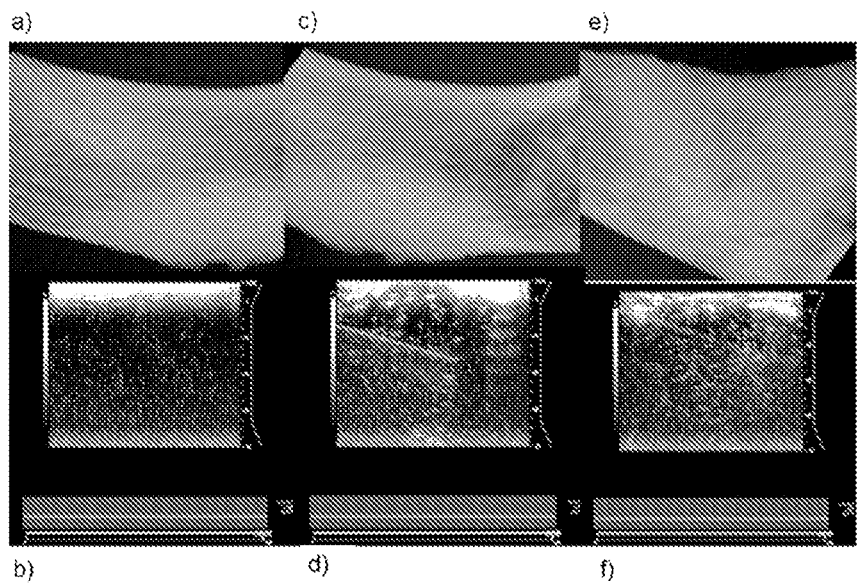
FIG. 9: shows an X-ray and ultra sound images undertaken on a human clavicle osteoporotic female bone; a) X-ray image before inducing a fracture on the human clavicle specimen, b) Ultra-sound image before inducing a fracture on the human clavicle specimen, c) X-ray image after inducing a fracture on the human clavicle specimen, d) Ultra-sound image after inducing a fracture on the human clavicle specimen, e) X-ray image after treatment with the pseudo-bone thermo-gel at the site of the fracture induced human clavicle specimen, f) Ultra-sound image after treatment with the pseudo-bone thermo-gel at the site of the fracture induced human clavicle specimen.

Ex-Vivo Evaluation of the Pseudo-Bone Thermo-Gel (the PEG-PCL-PEG:PPF:PF127 Thermoresponsive Hydrogel) Using Ultrasound and X-Ray Evaluation for Determination of Matrix Hardness and Matrix Resilience on Human Clavicle Bones:

Human clavicle bones were evaluated using X-ray, ultrasound, as well as textural analysis to determine the matrix hardness (MH) and matrix resilience (MR) of the bones before fracture, after fracture and after injecting the bones with the pseudo-bone thermo-gel (the PEG-PCL-PEG: PPF:PF127 thermoresponsive hydrogel) at the site of the induced 4 mm diameter butterfly fracture. Clavicular fractures are categorized by the site of injury. As seen in FIGS. 9a and 9b, an X-ray image and ultrasound image was captured before inducing a fracture respectively. Thereafter, another X-ray (FIG. 9c) and ultrasound (FIG. 9d) image was captured on the resulting fracture site. At this instance, the resulting bone appeared normal with a 4 mm diameter fracture at 2 positions (noted as darker portions in the X-ray (FIG. 9c) and white portions in the ultrasound image (FIG. 9d). These portions of the bones were then injected with the pseudo-bone thermo-gel and evaluated once more for acquiring X-ray (FIG. 9e) and ultrasound (FIG. 9f) images. After several images of various bones, the most defined images were selected for representation.

It can be clearly seen in the above mentioned images the distinct differences with the structural texture of the bone during the 3 stage procedure. The bones were then covered with a dialysis membrane, as to roughly mimic the periosteum layer of the bones. Thereafter the bone covered with the membrane was incubated in a shaker bath at a temperature of 37° C., with 50 rpm for 2 hours in PBS. The pseudo-bone thermo-gel was then injected at the site of the fracture, and left back to incubate in the same condition for 15 min. Following this stage, the membrane was then removed and the bones evaluated once more using X-ray (FIG. 9e) and ultrasound imaging (FIG. 9f). It can be clearly seen that the pseudo-bone thermo-gel penetrated deep into the sites of fracture, allowing adhesion and sealing of the fracture sites of the bone. As noted in the images, the X-rays appear much 'less dark' in FIG. 9e in comparison to FIG. 9c. Similarly, ultrasound images show sealing of the fracture site in FIG. 9f in comparison to the fracture line seen in FIG. 9d. This clearly demonstrates the highly temperature responsive nature of the pseudo-bone thermo-gel, providing a firm sealing of the fracture once injected.

The MH and MR of the bones were also evaluated. MR is the capacity of a given material to deform elastically, but revert to its usual state, once the force is removed. The average MH was calculated as 18.61 N/mm with a 9.48% MR before fracture. After inducing the fracture and injecting the bone with the thermo-gel system (MH and MR evaluation was undertaken 30 min after injecting and incubating the bone at 37° C. with the thermo-gel system), 18.3 N/mm MH and 9.28% MR was observed at the site of fracture, which was visibly lacking substantial bone material at the site when fractured. MR was calculated using a force-time profile, evaluating the ratio of the area under the curve (AUC), from peak to base, after eliminating the force initiated ($AUC_{2-3}$), over the baseline to peak, before removing the force ($AUC_{1-2}$), resulting in a % MR value. The gradient represents the flexibility and elastic property of the bone, whilst the AUC is the amount of deformation energy observed in the bone (Ellison et al., 2008).

It can thus be concluded that; even after inducing a fracture on the bone, following injection of the pseudo-bone thermo-gel, the fractured bone area displayed almost equivalent MH and MR to the original bone samples. The Applicant can therefore conclude that the pseudo-bone thermo-gel sealed the voids within the cracks of the fractured bone, allowing the bone the capacity to maintain significant mechanical integrity after treatment with the pseudo-bone thermo-gel. This is very advantageous.

In Vitro Analysis of the Pseudo-Bone Thermo-Gel (the PEG-PCL-PEG:PPF:PF127 Thermoresponsive Hydrogel):

Drug/API release studies were undertaken in different temperature conditions, to prove the thermo-responsive properties of the copolymer thermo-gel, thereby behaving as a controlled release formulation at body temperature, in comparison to a shorter duration of release at room temperature conditions. The range of PPF concentration used in the thermo-gel, was calculated determining the desirable strength required from the thermo-gel when exposed to physiological temperature condition.

Figure 10:
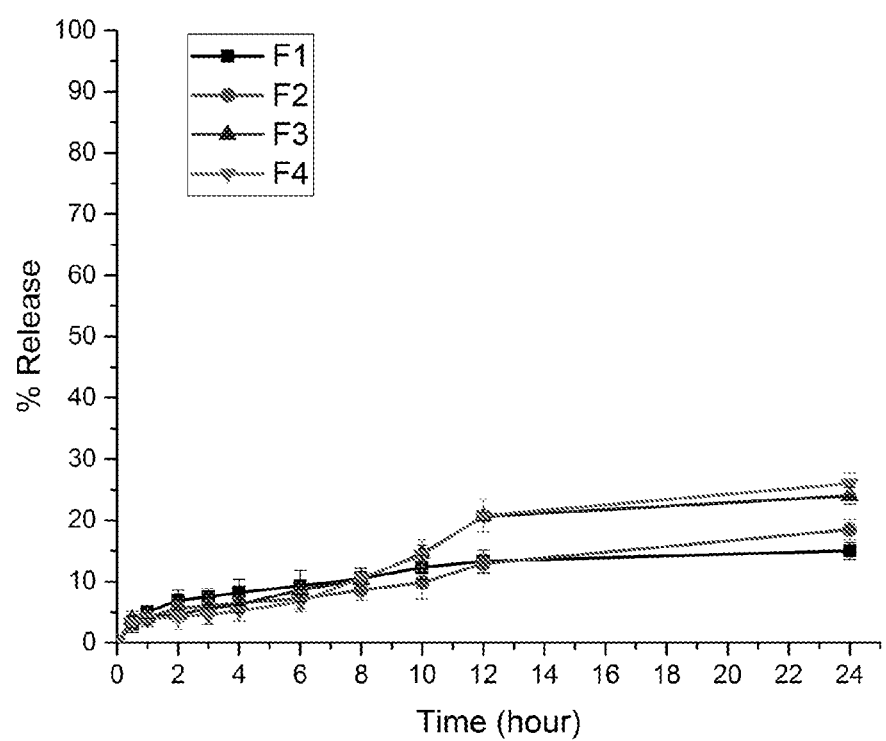
FIG. 10: shows an in vitro analysis of the pseudo-bone thermo-gel with variation in concentrations of % PPF and temperature conditions over 24 hours. F1 and F3 were blended as 8% $^w/_v$ PPF, and F2 and F4 as 20% $^w/_v$ PPF. F1 and F2 were evaluated at room temperature (±25° C.), F3 and F4 at body temperature (±37.5° C.).
Figure 11:
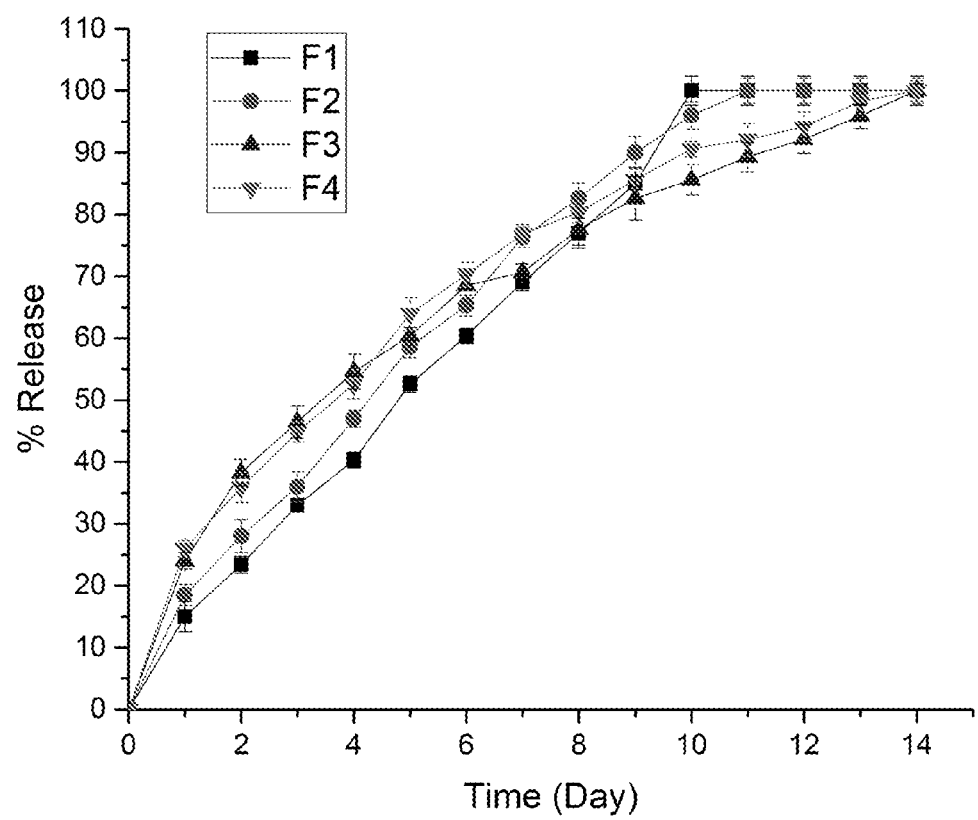
FIG. 11: shows an in vitro analysis of the pseudo-bone thermo-gel with variation in concentrations of % PPF and temperature conditions over 14 days. F1 and F3 were blended as 8% $^w/_v$ PPF, and F2 and F4 as 20% $^w/_v$ PPF. F1 and F2 were evaluated at room temperature (±25° C.), F3 and F4 at body temperature (±37.5° C.).

As seen in FIG. 10, all formulations displayed a gradual increase in drug release from 0 to 6 hours at both 25° C. and 37.5° C. Thereafter, formulations at body temperature conditions increased greater from 6 hours to 24 hours, compared to room temperature samples. Formulations F1 and F2 displayed an average release of up to 10 days. At this stage, the formulation displayed a semi-gelling composition, in comparison to an elastic-solid gel which is formed at body temperature (F3 and F4). As seen in FIG. 11, F3 and F4 released over 14 days, confirming the controlled release behaviour achieved with exposure to physiological temperature condition. This ideal gradual release of drug is an essential characteristic for obtaining desirable pharmacokinetic profiles, preventing spikes of drug release with unpredictable behaviour. The Applicant can thus conclude that the pseudo-bone thermo-gel (the PEG-PCL-PEG:PPF:PF127 thermoresponsive hydrogel) has significant potential for injectable drug delivery, forming an elastic solid-gel composition at body temperature, releasing a desirable uniformed drug concentration over a significant duration of patient therapeutic recovery time.

Conclusion:

A pseudo-bone thermo-gel (the PEG-PCL-PEG:PPF:PF127 thermoresponsive hydrogel) was synthesised and evaluated for its physico-chemical and mechanical properties. $^1$HNMR, ATR-FTIR and XRD studies confirmed successful copolymeric blending, using PEG-PCL-PEG, PPF and Pluronic® F127. The pseudo-bone thermo-gel demonstrated significant thermo-responsive properties, which was further affirmed using rheological and in vitro evaluation at varrying temperature conditions. A BCS class 2 drug, simvastatin was loaded in the thermo-gel, demonstrating significant drug release characteristics at body temperature over 14 days, compared to non-physiological temperature conditions, which displayed drug release for 10 days. Ex vivo analysis was undertaken using induced 4 mm diameter butterfly fractured human clavicle bones. These bones were analysed using X-ray, ultrasound and textural analysis, undertaken on the induced fractured bone before and after treatment of the thermo-gel. Results displayed significant bone filling, matrix hardening and matrix resilience properties, similar to the original density of the bone. It can thus be concluded that the developed pseudo-bone thermo-gel has significant potential for in vivo evaluation, with promising therapeutic benefits for treating small bone fractures.

REFERENCES

Attia, A. B. E., Yuin, Z., Hedrick, J. L., Lee, P. P., Ee, P. L. R., Hammond, P. T., Yang, Y., 2011. Mixed micelles self-assembled from block copolymers for drug delivery. Current Opinion in Colloid & Interface Science. 16, 182-194.

Basha, R. Y., Sampath Kumar, S., Doble, M., 2015. Design of biocomposite materials for bone tissue regeneration. Materials Science and Engineering. 57, 452-463.

Behravesh, E., Shung, A. K., Jo, S., Mikos, A. G., 2002. Synthesis and Characterization of Triblock Copolymers of Methoxy Poly(ethylene glycol) and Poly(propylene fumarate). Biomacromolecules. 3, 153-158.

Bosco, A. F., Faleiros, P. L., Carmona, L. R., Garcia, V. G., Theodoro, L. H., de Araujo, N. J., Nagata, M. J. H., de Almeida, J. M., 2016. Effects of low-level laser therapy on bone healing of critical-size defects treated with bovine bone graft. Journal of Photochemistry & Photobiology, B: Biology. 163, 303-310.

Caetano, G., Violante, R., Sant' Ana, A. B., Murashima, A. B., Domingos, M., Gibson, A., Bártolo, P., Frade, M. A., 2016. Cellularized versus decellularized scaffolds for bone regeneration. Materials Letters. 182, 318-322.

Caramella, C., Conti, B., Modena, T., Ferrari, F., Bonferoni, M. C., Genta, I., Rossi, S., Torre, M. L., Sandri, G., Sorrenti, M., Catenacci, L., Dorati, R., Tripodo, G., 2016. Controlled delivery systems for tissue repair and regeneration. Journal of Drug Delivery Science and Technology. 32, 206-228.

Cohn, D., Sosnik, A., Levy, A., 2003. Improved reverse thermo-responsive polymeric systems. Biomaterials. 24, 3707-14.

Denga, C., Wua, J., Chenga, R., Menga, F., Kloka, H., Zhong, Z., 2014. Functional polypeptide and hybrid materials: Precision synthesis via-amino acid N-carboxyanhydride polymerization and emerging biomedical applications. Progress in Polymer Science. 39, 330-364.

Egner, W., Egner, H., 2016. Thermo-mechanical coupling in constitutive modeling of dissipative materials. International Journal of Solids and Structures. 91, 78-88.

Ellison, C. D., Ennis. B. J., Hamad, M. L., Lyon, R. C., 2008. Measuring the distribution of density and tabletting force in pharmaceutical tablets by chemical imaging. J Pharm Biomed Anal. 48, 1-7.

Farokhi, M., Mottaghitalab, F., Shokrgozar, M. A., Ou, K., Mao, C., Hosseinkhani, H., 2016. Importance of dual delivery systems for bone tissue engineering. Journal of Controlled Release. 225, 152-169.

Ginés, J. M., Arias, M. J., Rabasco, A. M., Novák, C., Ruiz-Conde, A., Sanchez-Soto, P. J., 1996. Thermal characterization of polyethylene glycols applied in the pharmaceutical technology using differential scanning calorimetry and hot stage microscopy. Journal of thermal analysis. 46:1, 291-304.

Gioffredi, E., Boffito, M., Calzone, S., Giannitelli, S. M., Rainer, A., Trombetta, M., Mozetic, P., Chiono, V., 2016. Pluronic® F127 hydrogel characterization and biofabrication in cellularized constructs for tissue engineering applications. Procedia CIRP. 49, 125-132.

Gong, C. Y., Shi, S., Dong, P. W., Zheng, X. L., Fu, S. Z., Guo, G., Yang, J. L., Wei, Y. Q., Qian, Z. Y., 2009. In vitro drug release behaviour from a novel thermosensitive composite hydrogel based on Pluronic® F127 and poly(ethylene glycol)-poly(epsilon-caprolactone)-poly(ethylene glycol) copolymer. BMC Biotechnol. 9, 8-21.

Hashimoto, Y., Mukai, S., Sawada, S., Sasaki, Y., Akiyoshi, K., 2015. Thermo-gel tectonic porous gel loading biologics, nanocarriers, and cells for advanced scaffold. Biomaterials. 37, 107-115.

Hashimoto, Y., Mukai, S., Sawada, S., Sasaki, Y., Akiyoshi, K., 2015. Thermo-gel tectonic porous gel loading biologics, nanocarriers, and cells for advanced scaffold. Biomaterials. 37, 107-115.

He, S., Yaszemski, M. J., Yasko, A. W., Engel, P. S., Mikos, A. G., 2000. Injectable biodegradable polymer composites based on poly(propylene fumarate) crosslinked with poly(ethylene glycol)-dimethacrylate, Biomaterials. 21, 2389-2394.

Iwase, T., Morita, D., Ito, T., Takemoto, G., Makida, K., 2016. Favorable Results of Primary Total Hip Arthroplasty With Acetabular Impaction Bone Grafting for Large Segmental Bone Defects in Dysplastic Hips. The Journal of Arthroplasty. 31, 2221-2226.

Jeong, N., Park, J., Yoo, K., Kim, W., Kim, D., Yoon, S., 2016. Preparation, characterization, and in-vitro performance of novel injectable silanized-hydroxypropyl methylcellulose/phase-transformed calcium phosphate composite bone cements. Current Applied Physics. 16, 1523-1532.

Jo, S., Engel, P. S., Mikos, A. G., 2000. Synthesis of poly(ethylene glycol)-tethered poly(propylene fumarate) and its modification with GRGD peptide. Polymer. 41, 7595-7604.

Jung, Y., Park, W., Parka, H., Leeb, D., Na, K., 2017. Thermo-sensitive injectable hydrogel based on the physical mixing of hyaluronic acid and Pluronic® F-127 for sustained NSAID delivery. Carbohydrate Polymers. 156, 403-408.

Kasper, F. K., Tanahashi, K., Fisher, J. P. & Mikos, A. G. 2009. Synthesis of Poly(Propylene Fumarate). Nature protocols. 4:4, 518-525.

Khoshroo, K., Kashi, T. S. J., Mortarzadeh, F., Tahriri, M., Jazayeri, H. E., Tayebi, L., 2017. Development of 3D PCL microsphere/TiO2 nanotube composite scaffolds for bone tissue engineering. Materials Science and Engineering. 70, 586-598.

Lee, K., Wang, S., Lu, L., Jabbari, E., Currier, B. L., Yaszemski, M. J., 2006. Fabrication and Characterization of Poly(Propylene Fumarate) Scaffolds with Controlled Pore Structures Using 3-Dimensional Printing and Injection Moulding. Tissue Engineering. 12:10, 2801-2811.

LogithKumar, R., KeshavNarayan, A., Dhivya, S., Chawlal, A., Saravanan, S., Selvamurugan, N., 2016. A review of chitosan and its derivatives in bone tissue engineering. Carbohydrate Polymers. 151, 172-188.

Lucia, U., 2016. Econophysics and bio-chemical engineering thermodynamics: The exergetic analysis of a municipality. Physica A. 462, 421-430.

Luoa, Z., Yangc, Y., Dengb, Y., Suna, Y., Yangd, H., Wei, S., 2016. Peptide-incorporated 3D porous alginate scaffolds with enhanced osteogenesis for bone tissue engineering. Colloids and Surfaces B: Biointerfaces. 143, 243-251.

Lv, F., Mao, L., Liu, T., 2014. Thermosensitive porphyrin-incorporated hydrogel with four-arm PEG-PCL copolymer: Preparation, characterization and fluorescence imaging in vivo. Materials Science and Engineering. C 43, 221-230.

Ma, D., An, G., Liang, M., Liu, Y., Zhang, B., Wang, Y., 2016. A composited PEG-silk hydrogel combining with polymeric particles delivering rhBMP-2 for bone regeneration. Materials Science and Engineering. 65, 221-231.

Nayef, L., Mekhail, M., Benameur, L., Rendon, J. S., Hamdy, R., Tabrizian, M., 2016. A combinatorial approach towards achieving an injectable, self-contained, phosphate-releasing scaffold for promoting biomineralization in critical size bone defects. Acta Biomaterialia. 29, 389-397.

Nguyen, Q. V., Huynh, D. P., Park, J. H., Lee, D. S., 2015. Injectable polymeric hydrogels for the delivery of therapeutic agents: A review. European Polymer Journal. 72, 602-619.

Niu, G., Du, F., Song, L., Zhang, H., Yang, J., Cao, H., Zheng, Y., Yang, Z., Wang, G., Yang, H., Zhu, S., 2009. Synthesis and characterization of reactive poloxamer 407s for biomedical applications. J Control Release. 138, 49-56.

Pandit, N. K., Kisaka, J., 1996. Loss of gelation ability of Pluronic® F127 in the presence of some salts. Int J Pharm. 145, 129-36.

Rainer, A., Giannitelli, S. M., Accoto, D., DePorcellinis, S., Guglielmelli, E., Trombetta, M., 2012. Load-adaptive scaffold architecturing: a bioinspired approach to the design of porous additively manufactured scaffolds with optimized mechanical properties. Ann Biomed Eng. 40, 966-75.

Reginald-Oparaa, J. N., Attamaa, A., Ofokansia, K., Umeyorb, C., Kenechukwua, F., 2015. Molecular interaction between glimepiride and Soluplus1-PEG 4000 hybrid based solid dispersions: Characterisation and anti-diabetic studies. International Journal of Pharmaceutics. 496, 741-750.

Sanchez-Molina, D., Velazquez-Ameijide, J., Quintana, V., Arregui-Dalmasesa, C., Crandall, J. R., Subit, D., Kerrigan, J. R., 2013. Fractal dimension and mechanical properties of human cortical bone. Medical Engineering & Physics. 35, 576-582.

Santapuri, S., 2016. Thermodynamic restrictions on linear reversible and irreversible thermo-electro-magneto-mechanical processes. Heliyon. 2, 00164.

Schramm, G., 2004. A Practical Approach to Rheology and Rheometry. Thermo Electron (Karlsruhe), GmbH, Federal Republic of Germany. Volume 2.

Shung, A. K., Timmer, M. D., Jo, S., Engel, P. S. & Mikos, A. G. 2002. Kinetics of poly(propylene fumarate) synthesis by step polymerization of diethyl fumarate and propylene glycol using zinc chloride as a catalyst. Journal of Biomaterials Science, Polymer Edition. 13:1, 95-108.

Singh, A. K., Gajiwala, A. L., Rai, R. K., Khan, M. P., Singh, C., Barbhuyan, T., S. Vijayalakshmi, S., Chattopadhyay, N., Sinha, N., Kumar, A., Jayesh, R., 2016. Cross-correlative 3D micro-structural investigation of human bone processed into bone allografts. Materials Science and Engineering. C 62, 574-584.

Sun, K. H., Sohn, Y. S., Jeong, B., 2006. Thermogelling poly(ethylene oxidebpropylene oxide-b-ethylene oxide) disulfide multiblock copolymer as a thiolsensitive degradable polymer. Biomacromolecules. 7, 2871-7.

Tang, D., Tare, R. S., Yang, L., Williams, D. F., Ou, K., Oreffo, R. O. C., 2016. Biofabrication of bone tissue: approaches, challenges and translation for bone regeneration. Biomaterials. 83, 363-382.

Tanga, Z., Hea, C., Tiana, H., Dinga, J., Hsiaob, B. S., Chub, B., Chen, X., 2016. Polymeric nanostructured materials for biomedical applications. Progress in Polymer Science. 60, 86-128.

Timmer, M. D., Ambrose, C. G., Mikos, A. G., 2003. In vitro degradation of polymeric networks of poly(propylene fumarate) and the crosslinking macromer poly(propylene fumarate)-diacrylate, Biomaterials. 24, 571-577.

Vandenhaute, M., Schelfhout, J., Van Vlierberghe, S., Mendes, E., Dubruel, P., 2014. Cross-linkable, thermo-responsive Pluronic® Ö building blocks for biomedical applications: Synthesis and physico-chemical evaluation. European Polymer Journal. 53, 126-138.

Volkmer, E., Leicht, U., Moritz, M., Schwarz, C., Wiese, H., Milz, S., Matthias, P., Schloegl, W., Friess, W., Goettlinger, M., Augat, P., Schieker, M., 2013. Poloxamer-based hydrogels hardening at body core temperature as carriers for cell based therapies: in vitro and in vivo analysis. J Mater Sci Mater Med. 24, 2223-34.

Wei, Z., Hao, J., Yuan, S., Li, Y., Juan, W., Sha, X., Fang, X., 2009. Paclitaxel-loaded Pluronic® P123/F127 mixed polymeric micelles: Formulation, optimization and in vitro characterization. International Journal of Pharmaceutics. 376, 176-185.

Yin, G., Chen, G., Zhou, Z., Li, Q., 2015. Modification of PEG-b-PCL block copolymer with high melting temperature by the enhancement of POSS crystal and ordered phase structure, RSC Advances, RSC Adv. 5, 33356.

Zhang, W., Shi, Y., Chen, Y., Ye, J., Sha, X., Fang, X., 2011. Multifunctional Pluronic® P123/F127 mixed polymeric micelles loaded with paclitaxel for the treatment of multidrug resistant tumors. Biomaterials. 32, 2894-2906.

Zhao, L., Li, X., Zhao, J., Ma, S., Ma, X., Fan, D., Zhu, C., Liu, Y., 2016. A novel smart injectable hydrogel prepared by microbial transglutaminase and human-like collagen: Its characterization and biocompatibility. Materials Science and Engineering. 68, 317-326.

Zhou, S., Deng, X., Yang, H., 2003. Biodegradable poly(ε-caprolactone)-poly(ethylene glycol) block copolymers: characterization and their use as drug carriers for a controlled delivery system. Biomaterials. 24:20, 3563-70.

Zhou, Q., Zhang, Z., Chen, T., Guo, X., Zhou, S., 2011. Preparation and characterization of thermosensitive Pluronic® F127-b-poly(e-caprolactone) mixed micelles, Colloids and Surfaces B: Biointerfaces. 86, 45-57.

Example 2

Experimental

Synthesis of an Ink in Accordance a Fifth Aspect of this Invention:

An ink, typically a bioink, for a three dimensional (3D) printer is manufactured from the PEG-PCL-PEG:PPF:PF127 thermoresponsive hydrogel described in the first aspect of this invention and particularly in Example 1 above.

Materials and Methods

Materials

PEG (Mw 4000), stannous octoate, 92.5%; Pluronic® F-127; poly(ethylene glycol) diacrylate; epsilon-caprolactone, 99%; petroleum ether, 90%; and simvastatin (molecular weight: 418.57), 97% purity, were procured from Sigma-Aldrich (St. Louis, Mo., USA). Methanol, 99%; diethyl fumarate, 98%; diethyl ether (anhydrous); hydroquinone, 99% purity; methylene chloride; propylene glycol (1,2-propandiol); hydrochloric acid, 1.85% $^v/_v$; sodium sulphate and zinc chloride were purchased from Merck (Pty) Ltd. All other reagents were of analytical grade and were employed as received. All reactions were undertaken under inert conditions.

Synthesis of the Bio-Ink Formulation

A strategically designed copolymeric blend of polymers; polypropylene fumarate (PPF), PEG-PCL-PEG, and Pluronic® PF 127, was optimized to provide the PEG-PCL-PEG:PPF:PF127 thermoresponsive hydrogel for 3D bio-printing and loaded with simvastatin drug.

In brief, PPF was prepared by reacting 30.52 g, (180 mmol) of diethyl fumarate and 40.75 g (540 mmol) of propylene glycol, employing a round bottom flask (RBF), under inert conditions, at 90° C. To this reaction, under constant magnetic stirring, the crosslinking inhibitor hydroquinone (0.0303 g, 0.266 mmol), and the Lewis acid catalyst $ZnCl_2$ (0.2 g, 1.53 mmol) was added. The temperature was then increased and maintained at 130° C., over the next 3 hours, yielding the intermediate product of bis(hydroxypropyl) fumarate and ethanol (distillate). This reaction step was then ceased when 90% of the theoretical ethanol was collected in the receiving flask. The following step involved the transesterification of bis(hydroxypropyl) fumarate, carried out under vacuum conditions (<1 mmHg), at 130° C. to yield PPF and ethanol as the by-product. PPF polymer was then purified, removing the catalyst, dissolving in dichloromethane (DCM), and washing twice with 1.85% $^w/_v$ solution of HCl. Repeated washes with distilled water and brine solution and drying with anhydrous sodium sulphate was then undertaken. DCM was removed using rotary evaporation, and chilled diethyl ether solution was employed for removal of excess hydroquinone from the PPF precipitate, with resuspension in DCM under vacuum conditions, to further purify the polymer [19]. PPF was then stored and used as required in the following reaction.

Free radical polymerization was undertaken for preparation of copolymer PEG-PCL-PEG, using PEG (Mw 4000) as the macro initiator and catalyst stannous octoate ($Sn(Oct)_2$). Briefly, 0.007M of PEG 4000 and 0.098M of ε-caprolactone was reacted in a round bottom flask, purged with nitrogen, at a temperature of 125° C., under constant magnetic stirring (3500 rpm). 100 μL of the catalyst was then added to the reaction, and left for 6 hours under nitrogen purging. PPF (8% $^w/_v$-20% $^w/_v$) and PF127 (14% $^w/_v$-16% $^w/_v$) was then added to the reaction, specifying the concentrations as obtained by the designed formulations using MATLAB® programming. The reaction temperature was then increased to 140° C., and left for 6 hours under constant magnetic stirring of 3000 rpm. The reaction was then allowed to cool to room temperature, further adding DCM, and washed thrice with distilled water. The organic solvent was then removed using rotary evaporation, and stored at 10° C. for further use before 3D bio-printing. Simvastatin drug was then loaded in the PEG-PCL-PEG:PPF:PF127 thermoresponsive hydrogel, with a therapeutic dose calculated at 10 mg loaded per scaffold. The dose for loading was calculated backwards according to the material required for bio-printing, dependant on parameters employed, according to the optimization of fabrication procedures on the bio-printed scaffold.

A bio-ink paste was then formed by adding a ratio of 6:3:1 of the PEG-PCL-PEG:PPF:PF127 thermoresponsive hydrogel: methanol: distilled water respectively. (This could be done with or without drug/API loading.)

The bio-ink then underwent microwave assisted heating using a specific laboratory designed MAS-II Plus Microwave Synthesis Workstation Sineo, China; at 50° C. for 10 min, at 600 watts, increasing the viscous nature of the bio-ink, allowing each layer of the scaffold when printing, to dry easier and build on each platform effectively.

Artificial Neural Network Design and Optimization of the 3D Bio-Printed Scaffold:

Artificial neural network can be used to determine linear and non-linear sophisticated relationships between dependant and independent variables in a study [20]. The fundamental benefit of using ANN, is the capacity for the neural network to learn directly from an informal dataset, that has not been associated directly to a mathematical equation. Herein below, MATLAB Simulink® R2016a edition (The MathWorks, Inc.) was employed to undertake neural networking.

Formulations were derived using variables of 14% $^w/_v$-16% $^w/_v$ of PF127 and 8% $^w/_v$-20% $^w/_v$ of PPF. Formulations were obtained using MATLAB®, determining formulation combination of integer matrices, in 1% $^w/_v$ concentration increment, within the variable range of PPF and PF127. The concentrations of PEG-PCL-PEG polymer, and all other reagents were kept constant during the design of the study. A total of 39 formulations were derived and synthesised using this software, as seen in Table 1. All formulations were evaluated for parameters of temperature of gelation before bio-printing and the duration of release after bio-printing. This was then analysed as a factor (Equation 1), with the highest factor representing the optimized formulation matrix.

$$\text{Factor} = \frac{tg}{bt} \times Rd \quad (1)$$

Where tg represents the thermo-gelation temperature of the synthesised copolymer, bt representing body temperature and Rd representing the release duration. Performance training of the neural network was evaluated by the mean square error and regression analysis.

A designed network, using a multilayer feed forward-back propagation, containing an input, output, as well as a variety of hidden layers, refers to a system architecture where the gradient is computed for multilayer nonlinear networks. This back propagation relationship, thus uses large input and output datasets, to determine a network mapping, thereby not requiring a definite mathematical equation to undertake the modeling. This gradient descent algorithm using back propagation is classified as the Widrow-Hoff learning rule, using multiple-layer networks, with various degrees of optimization to the algorithm.

A training percentage of 70% was selected in the network, and the network was adjusted according to its resulting error obtained. A validation of 15% was undertaken, measuring the network generalization, thereby terminating training when generalization of the network stops improving. A testing percentage of 15% was programmed, resulting in no effect on training parameters, providing an indication of independent measure of performance during and after training of the network. Thus, this complies to 100% evaluation split in 3 categories of network priority. The algorithm employed in a study, depends on the complexity of variables and desired strategic outcome of modeling. In this study, we used 3 types of algorithms, such as; Levenberg-Marquardt, Scaled Conjugate Gradient and Bayesion Regulization. The algorithm which obtained the best training results, was employed for the ANN study.

In terms of expressing data in the form equation variables, the input to hidden layer U, was expressed by:

$$(U)=(W)(I) \quad (2)$$

W, representing the weight, and I the input. Each term of the hidden layer matrix can be explained as follows:

$$Uj=\Sigma_{i=1}^{n} Wili-\Theta \quad (3)$$

Θ, representing the associated bias. Optimization in the hidden layer using transfer functions was conducted. Non-linear functions {log-sigmoid (log sig), hyperbolic tangent sigmoid function (tan sig)} and linear function (purelin), was undertaken to investigate the ability of optimum results. Equations (4), (5) and (6) can be used to understand the sequencing of optimization of the network:

$$f(U) = u \quad (4)$$

$$F(U) = \frac{1}{[1+e^{(-u)}]} \quad (5)$$

$$f(U) = \frac{2}{[1+e^{(-2u)}]-1} \quad (6)$$

As means of determining the effectiveness of the models, determination coefficient ($R^2$), and the mean square error (MSE), was employed as follows:

$$MSE = \frac{1}{n} = \sum_{i=1}^{n}(Y \text{ response predicted} - Y \text{ response experimental})^2 \quad (7)$$

$$R^2 = 1 - \frac{\sum_{i=1}^{n}(Y \text{ response predicted} - Y \text{ response experimental})^2}{\sum_{i=1}^{n}(Y \text{ response experimental} - Y \text{ response mean})^2} \quad (8)$$

The adaptation learning function employed was the gradient descent, with momentum weight and bias learning function. Optimization of the learning function also varied with the number of neurons, resulting in observational learning with greater percentage validity. Parameters of the number of epochs, minimum gradient and Mu employed was evaluated at $10^2$, $1^{-10}$ and 0.01 respectively.

Thermo-gelation analysis was undertaken on all 39 designed formulations using a Modular Advanced Rheometer (ThermoHaake MARS Modular Advanced Rheometer, Thermo Electron, Karlsruhe, Germany), comprising a C35/1° Ti sensor. A temperature range of 10° C.-40° C. was conducted, using a cone and plate inertia of $1.721 \times 10^{-6}$ kg m$^2$, analysing 5 mL of sample. The sample was analysed in the range of 0-1.0 Hz, in the region of the shear independent plateau of the strain amplitude sweep stress (11). G', representing the effects of elastic energy (storage modulus), and G", representing the effects of viscous energy (loss modulus) was evaluated. The point of thermo-gelation occurred when the fluid nature of the gel (G") transitioned to a semi-solid composition (G'), being subjected to an increase in temperature, over constant sinusoidal oscillation.

TABLE 1

Design specifications of the 3D bio-printed scaffold formulations using MATLAB Simulink ®.

| Formulation Number | Percentage PPF w/v | Percentage PF-127 w/v |
|---|---|---|
| 1 | 8 | 14 |
| 2 | 9 | 14 |
| 3 | 10 | 14 |
| 4 | 11 | 14 |
| 5 | 12 | 14 |
| 6 | 13 | 14 |
| 7 | 14 | 14 |
| 8 | 15 | 14 |
| 9 | 16 | 14 |
| 10 | 17 | 14 |
| 11 | 18 | 14 |
| 12 | 19 | 14 |
| 13 | 20 | 14 |
| 14 | 8 | 15 |
| 15 | 9 | 15 |
| 16 | 10 | 15 |
| 17 | 11 | 15 |
| 18 | 12 | 15 |
| 19 | 13 | 15 |
| 20 | 14 | 15 |
| 21 | 15 | 15 |
| 22 | 16 | 15 |
| 23 | 17 | 15 |
| 24 | 18 | 15 |
| 25 | 19 | 15 |
| 26 | 20 | 15 |
| 27 | 8 | 16 |
| 28 | 9 | 16 |
| 29 | 10 | 16 |
| 30 | 11 | 16 |
| 31 | 12 | 16 |
| 32 | 13 | 16 |
| 33 | 14 | 16 |
| 34 | 15 | 16 |
| 35 | 16 | 16 |
| 36 | 17 | 16 |
| 37 | 18 | 16 |
| 38 | 19 | 16 |
| 39 | 20 | 16 |

Figure 12:
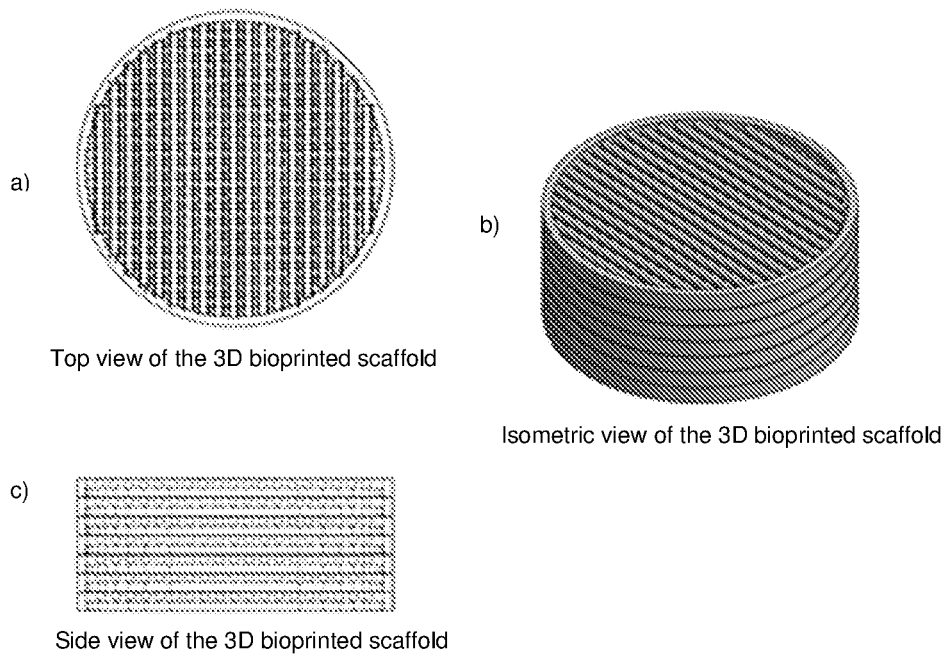
FIG. 12: shows a CAD specification design of the optimized 3D bio-printed scaffold.

3D Design of the Bio-Printed Pseudo-Bone Drug Delivery Scaffold:

The 3D bioprinted scaffold was designed using Autodesk Inventor®, 3D computer-aided design (CAD), for precise fabrication prototyping, of the polymer based biomaterial. The scaffold was designed as a cylindrical implant, with dimensions comprising 16 mm radius and a height of 4.2 mm After generating a Stereolithography (STL) file on Inventor®, this file was imported to EnvisionTEC Visual Machines software, thereby converting to a Borland Package Library (BPL) file for bio-printing processing. Design of internal features and uniform slicing of the design was then undertaken on this software, printing a strand diameter of 500 μm, and creating an inner structure pattern between layers at 30°. The scaffold was designed with a total number of 7 layers, with the height of each layer being 0.6 mm A 3D Bioplotter® (EnvisionTEC GmbH, Gladbeck, Germany) was employed, using a pressure and temperature regulated syringe, with parameters optimized at 1.0 bar of pressure, speed at 1 mm/s and syringe temperature regulated at 20° C. The temperature of the printing platform was maintained at 40° C. The transfer height and needle offset was set at 5 mm and 0.5 mm respectively. Pre flow delay, post flow delay and time between layers were set as 0, 0 and 120 sec respectively. The low pressure and speed of printing, provided sufficient time for the structure to solidify, thereby promoting accuracy and scaffold platform building to occur. This technology allows development of any object to be printed, provided the appropriate uniform viscosity is maintained throughout. FIG. 12 illustrates the CAD design of the 3D bioprinted scaffold model.

Chemical and Thermal Evaluation of the 3D Bioprinted Pseudo-Bone Scaffold:

Nuclear magnetic resonance (NMR) was undertaken on the 3D printed scaffold using a Bruker AVANCE II 500 MHz (Bruker Avance Biospin, Germany) instrument. Deuterated chloroform ($DCl_3$) was used to dissolve the scaffold, evaluating the sample at 25° C.

Thermogravimetric analysis was undertaken using a TGA 4000 thermogravimetric analyzer (PerkinElmer Inc, Massachusetts, USA), with temperature range of 30° C.-900° C. This was undertaken at a ramping rate of 10° C./min, under inert conditions, with a purge rate of 20 mL/min of nitrogen. A sample weight of 10 mg was used, evaluating the percentage degradation of the 3D bioprinted scaffold. The 1$^{st}$ derivative was obtained after analysis of the thermogram, detecting the point of inflection for analysis. This peak indicates the point of greatest rate of change of the 3D bioprinted scaffold, with most significant weight loss observed.

Morphological Analysis Undertaken on the 3D Bio-Printed Pseudo-Bone Scaffold:

Scanning electron microscopy (SEM) analysis was undertaken to confirm the porosity nature of the 3D bio-printed scaffold, as well as to determine the accuracy of bio-printing parameters in relation to morphological characteristics between all 7 layers of the 3D scaffold. The 3D bio-printed scaffold sample was prepared by sputter coating on an aluminium spud, employing an EPI sputter coater (SPI Module™ sputter-coater and control unit, West Chester, Pa., USA). The sample was then analysed using a FEI ESEM Quanta 400F (FEI™, Hillsboro, Oreg., USA) electron microscope, with an electron acceleration charge of 20 kV, producing high resolution images of the 3D bio-printed scaffold.

In Vitro Evaluation Undertaken on the Designed 3D Bioprinted Pseudo-Bone Drug Delivery Scaffolds:

All 39 design formulations (n=3) were evaluated, employing a dialysis membrane (MWCO: 1.2 kDa), immersed in phosphate buffer solution (PBS, pH 6.8). All samples were evaluated at sink conditions, employing an orbit shaker incubator (LM-530-2, MRC Laboratory Instruments Ltd, Hahistadrut, Holon, Israel) at 37.5° C., 50 rpm. 1 mL of sample was removed at each time point from the buffer, and replaced equally with new buffer. Release samples were then analysed for simvastatin concentration using a UV spectrophotometer, at wavelength 238 nm (IMPLEN Nanophotometer™, Implen GmbH, München Germany) This was undertaken using a 10 times dilution factor of path-length 0.1 mm [21].

Matrix Testing Undertaken on the 3D Bio-Printed Pseudo-Bone Scaffold:

Matrix hardness (MH) and matrix resilience (MR) employing a textual analyzer (TA.XTplus, Stable Microsystems, Surrey, UK), under parameters of temperature at 37.5° C. and pressure of 1 atm, was undertaken on a healthy human clavicle bone, and thereafter on the area of the bone which was fractured and treated with the 3D bio-printed scaffold. A steel flat tip probe of 2 mm diameter was used to determine MH and for MR evaluation, a steel cylindrical probe of 50 mm diameter was employed. The clavicles were induced with a 4 mm diameter fracture in the region between the cervical fascia and the area bellow the conoid tubercle [22]. This was undertaken using a 4 mm punch and dye apparatus, with a hydraulic pressure of 0.6 MPa. The fracture induced human clavicle bone was then tested after incubation at 37.5° C. for 2 hours, applying 2 mL of phosphate buffer on the scaffold, at the fracture site, evaluating the properties of matrix hardness and resilience on the bone thereafter.

Figure 13:
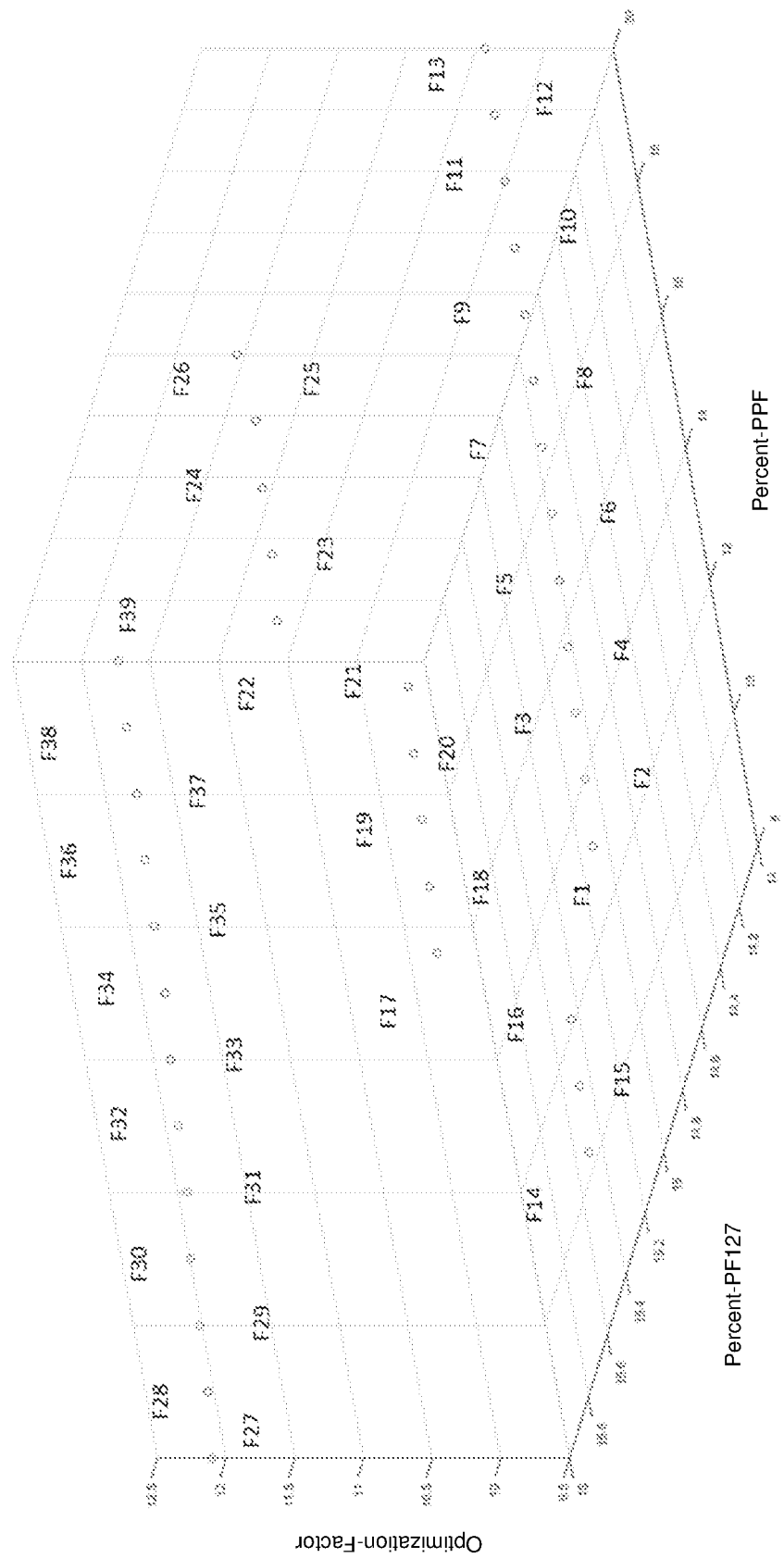
FIG. 13: shows a 3D representation of the designed formulations, reflecting the percentage of PPF and PF127, with the optimization factor for each formulation.
Figure 15:
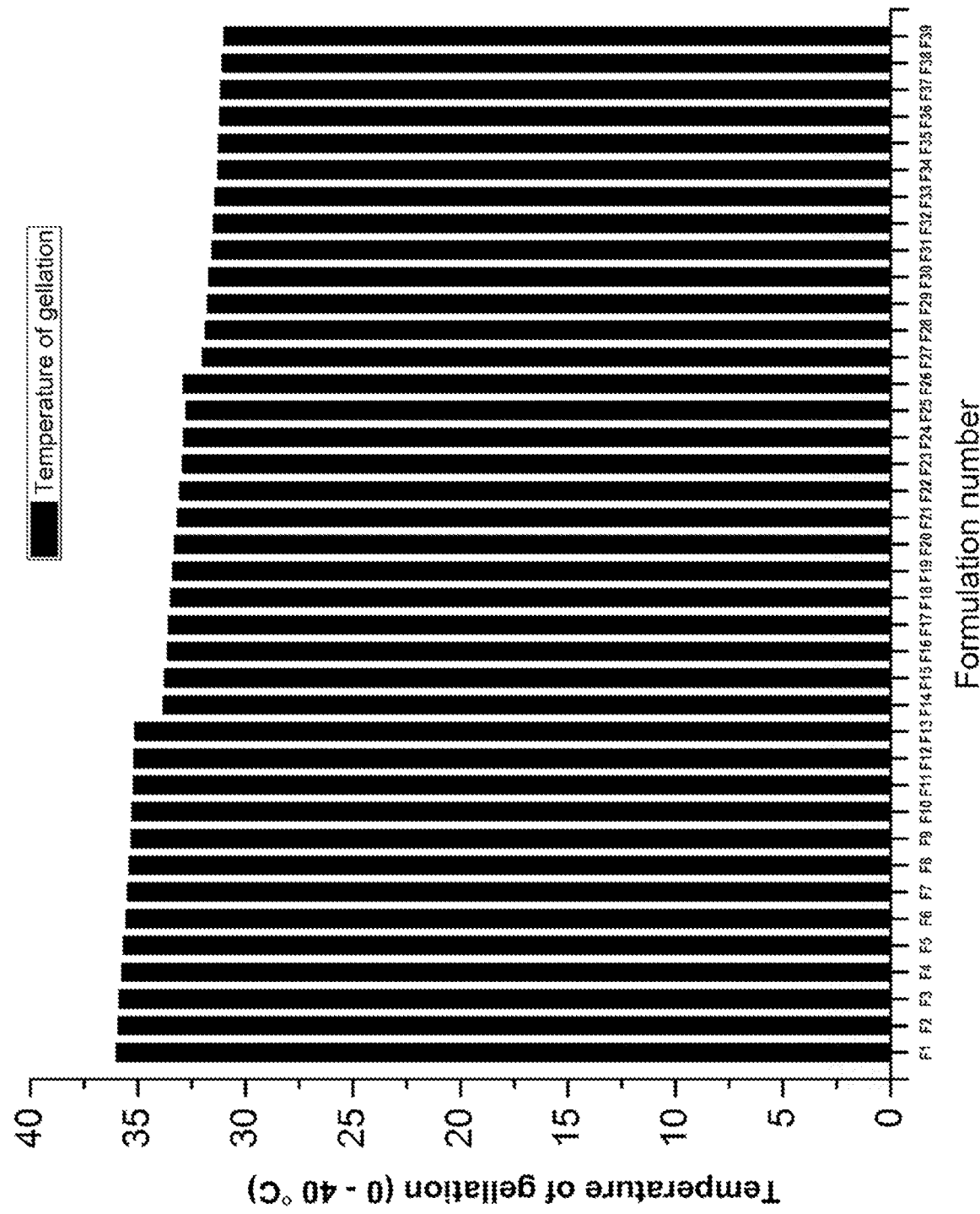
FIG. 15: shows a temperature of gelation representation of the 39 designed formulations evaluated in the study before 3D printing.

Results and Discussion (Example 2):

Design and Optimization of the 3D Bioprinted Pseudo-Bone Drug Delivery Scaffold Employing Artificial Neural Network Application:

The 3D bio-printed scaffolds, evaluated as 39 design formulations using MATLAB® programming, comprised of variables of PPF (8% $^w/_v$-20% $^w/_v$) and PF127 (14% $^w/_v$-16% $^w/_v$), as seen in Table 1. These design scaffold formulations were studied in response to duration of release of simvastatin and the degree of thermo-gelation before 3D printing. FIG. 13 reflects the formulation compositions and response factor from each programmed design, using a 3D Simulink design graph. It was observed that as the concentration of PPF increased, greater concentration of simvastatin was released within 24 hours in the formulations. This can be attributed to simvastatin, a biopharmaceutics classification system (BCS) class 2 drug, encapsulated within regions of hydrophobic chains of PPF. It was also observed that, as PF127 variable increased, the scaffolds biodegraded over a greater time duration, significantly controlling the release rate of the loaded drug further. This slower sustained release effect of PF127 in the formulation is essential for implants and delivery of hydrophobic drugs [23]. The formulations however demonstrated a decrease in gelation temperature as the concentration of PF127 was increased, as seen in FIG. 15.

Providing these inputs in the program, Equation 1 was employed in determining the variable concentrations for the optimized formulation, thereafter training these inputs using ANN. The 546 number data set involved in the study was undertaken by varying the number of neurons in the hidden layer, using the sigmoid symmetric transfer function and using 3 different training functions for developing the model. The optimum network was derived using performance indicators of error function and $R^2$ values. A variation in the number of neurons in the hidden layer is an essential component in ANN. The network thus becomes underperforming or highly entangled to sort, when the number of neurons are too high or low. Thus, a region between 6-16 neurons was investigated, and considered an efficient model for optimum results. The optimum number of neurons after testing was found to be 10, thus producing the lowest mean square error and highest regression values for various training models.

For training of the network, the feed forward back propagation method was employed. Using the Levenberg-Marquardt, Bayesian Regularization and Scaled conjugate gradient training networks, we could evaluate which training network resulted in the lowest error functions (Equation 7) and highest regression value (Equation 8). After much training and evaluation of input data, the Levenberg-Marquardt training function was observed to be the most effective algorithm employed using the sigmoid (tansig) function. Table 2 reflects the results obtained from the training algorithm and parameter performance observed.

TABLE 2

Training functions undertaken for optimization of the designed formulations

| Training Algorithm | Mean Square Error (MSE) | Regression Function ($R^2$) |
| --- | --- | --- |
| Levenberg- Marquardt | ≤0.1 | 9.99 |
| Bayesian Regularization | ≤0.1 | 9.82 |
| Scaled conjugate gradient | 0.7 | 9.14 |

Figure 14:
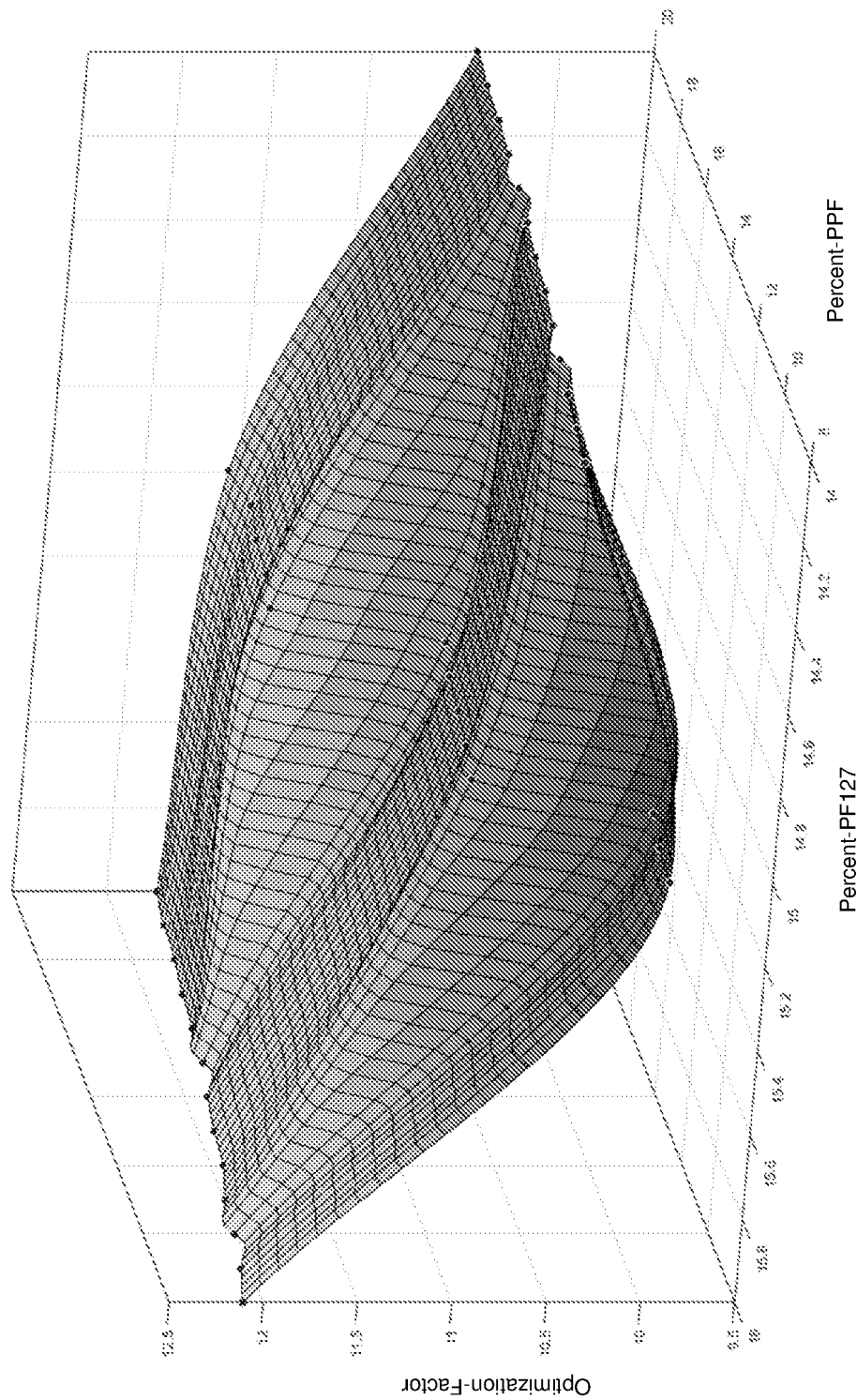
FIG. 14: shows a 3D representation of the designed formulations using a cubic function surface plot, with the highest point on the surface plot representing the optimum polymer concentrations.

FIG. 14 reflects a 3D cubic function of optimization parameters using a surface computed plot. The optimized formulation with the greatest factor, representing an optimum ratio of release duration and thermo-gelation was found to be 14% $^w/_v$ of PPF and 16% $^w/_v$ of PF127. This optimized formulation composition was thus selected as the superior formulation specification. FIG. 15 represents the thermo-gelation temperature of the 39 formulations, representing a decrease in gelation temperature as the concentration of PF127 was increased.

Figure 16:
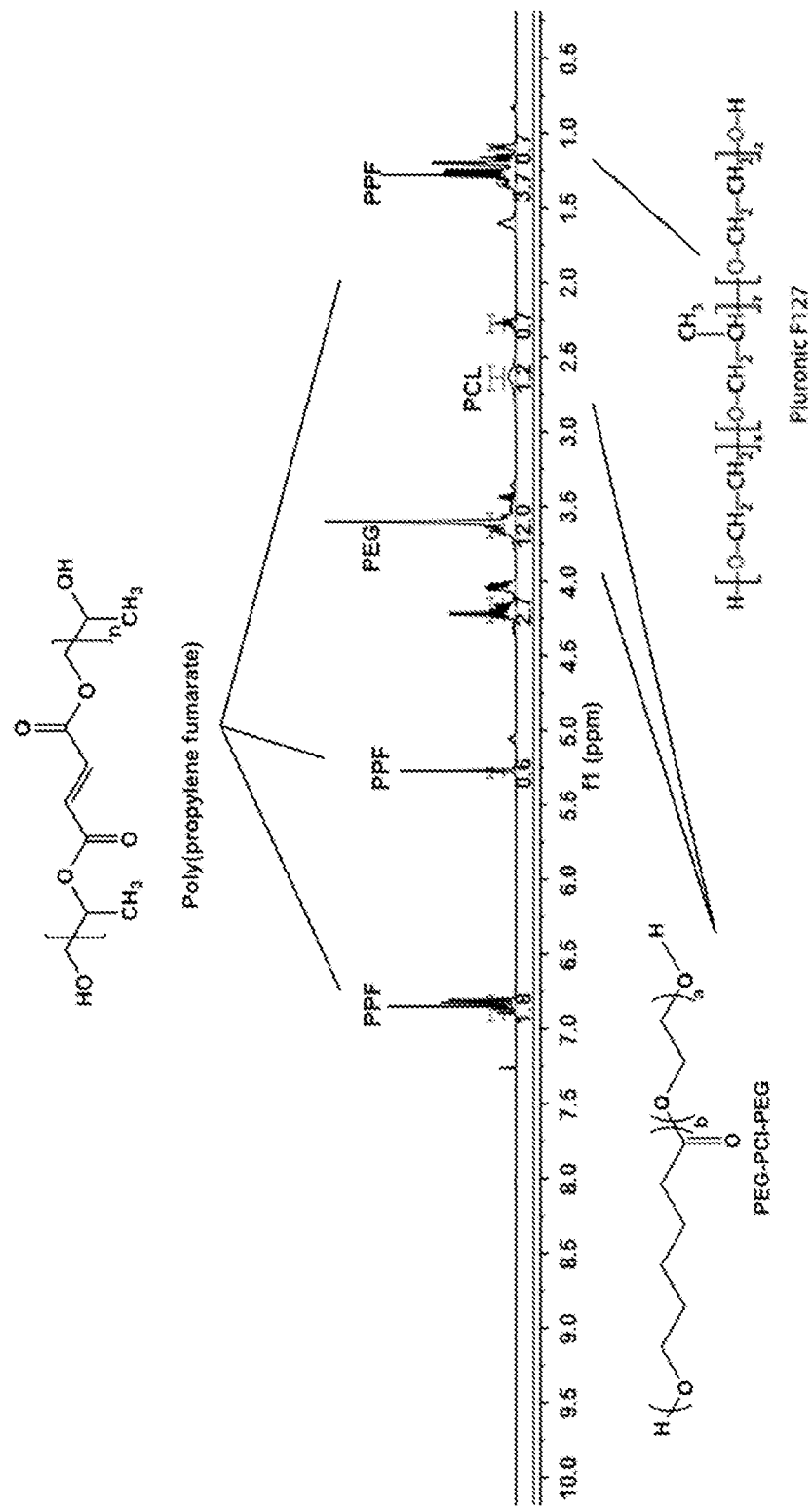
FIG. 16: shows an NMR analysis of the 3D bio-printed pseudo-bone scaffold, reflecting chemical shifts and copolymeric composition.

Chemical and Thermo-Gravimetric Analysis of the Optimized 3D Bioprinted Pseudo-Bone Scaffold:

NMR analysis was undertaken on the 3D bio-printed scaffold, evaluating each chemical component in the formulation. As seen in FIG. 16, the broad signal peaks in the region of 3.5 ppm and 3.65 ppm represents the —($CH_2$)— functional groups present in PEG, with PCL functionalities of —OCCH$_2$— and —CH$_2$OOC— in the regions of 1.6 ppm and 2.2 ppm respectively. Evaluating peaks responsible for PPF, it was evident that this defined functionalities of —HC═CH— in the region of 6.75 ppm remained intact in the PPF backbone structure. The —CH$_3$— functionalities of PF127 was identified in the region of 1.1 ppm, with further evaluation reflecting no chemical shifting of this functionality of protons in the backbone of PEG-PCL. The peaks observed in regions 1 ppm-1.3 ppm can thus be attributed to the —CH$_3$— groups found in PPF and PF127, responsible for chemical shifts from the parent compounds respectively. Peaks for PF127 was also reflected in the region of 3.4 ppm, reflecting protons of individual functional groups. Minor peaks of PPF, not reflected in the 3D bio-printed scaffold, suggests successful copolymeric blending interaction, resulting in the end groups of the PPF polymeric chain eliminated [24, 25, 26].

Figure 17:
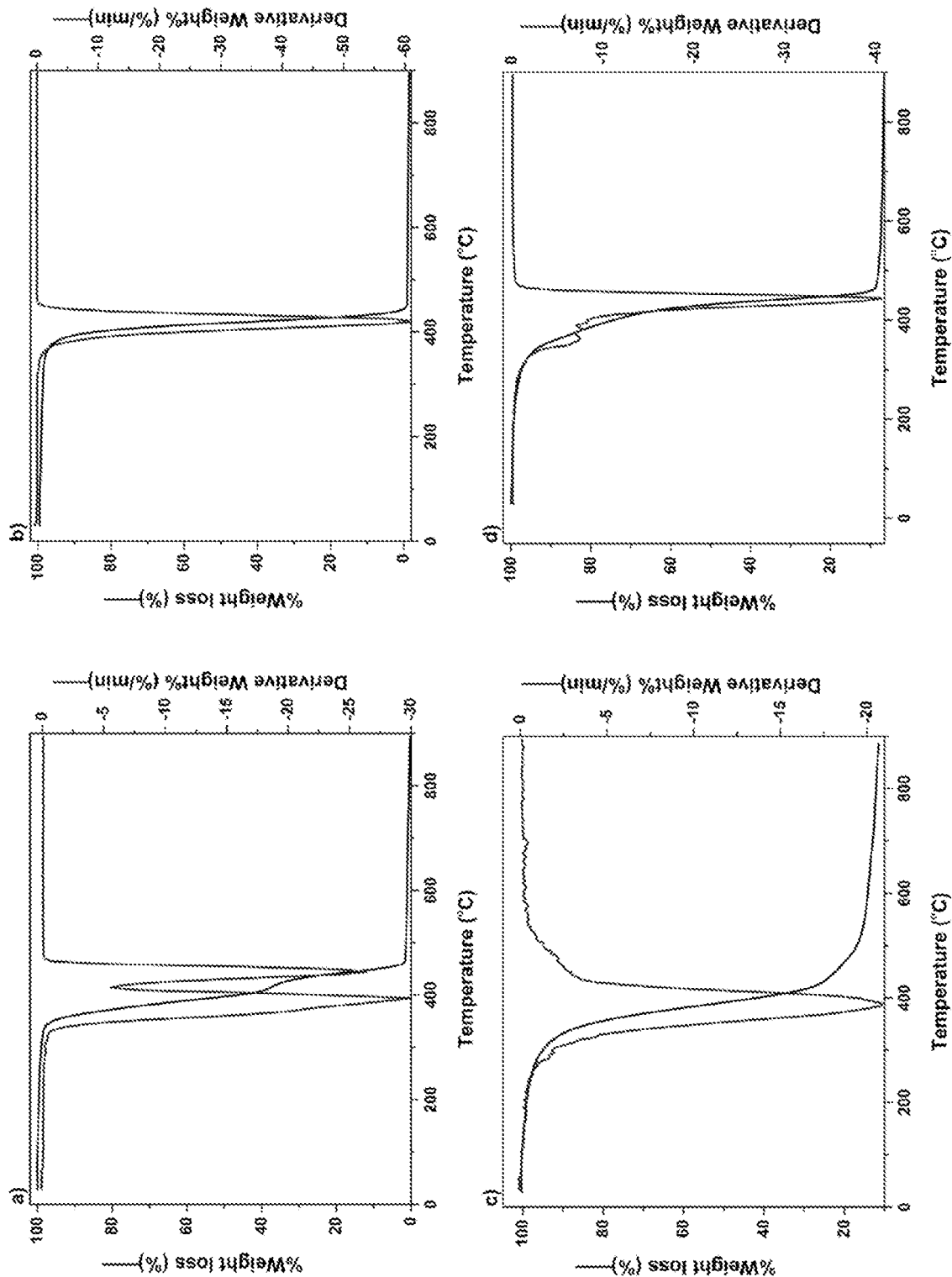
FIG. 17: shows a TGA analysis undertaken in the region of 30° C. to 900° C. for a) PEG-PCL-PEG, b) PF127, c) PPF and d) 3D bio-printed scaffold.

Thermo-gravimetric analysis was undertaken to determine the temperature range, resulting in the greatest weight loss experienced in the 3D bio-printed scaffold, after being exposed to a temperature of 30° C.-900° C. FIG. 17a represents polymer PEG-PCL-PEG, producing a double point of inflection, with the maximum degradation for PEG and PCL chains found in the region of 387° C. and 448° C. respectively. An initial percentage of degradation below 100° C. was attributed to the release of moisture in the sample, due to the hygroscopic nature of the polymer. PF127 demonstrated significant biodegradation in the range of 412° C., with PPF reflecting substantial weight loss at 379° C., as seen in FIG. 17b and FIG. 17c respectively. FIG. 17d represents the 3D bio-printed pseudo-bone scaffold. As observed, the point of inflection represented at 448° C., was observed with greater thermal stability compared to individual polymers, possibly modified due to properties of increasing interfacial adhesion in the scaffold matrix.

Figure 18:
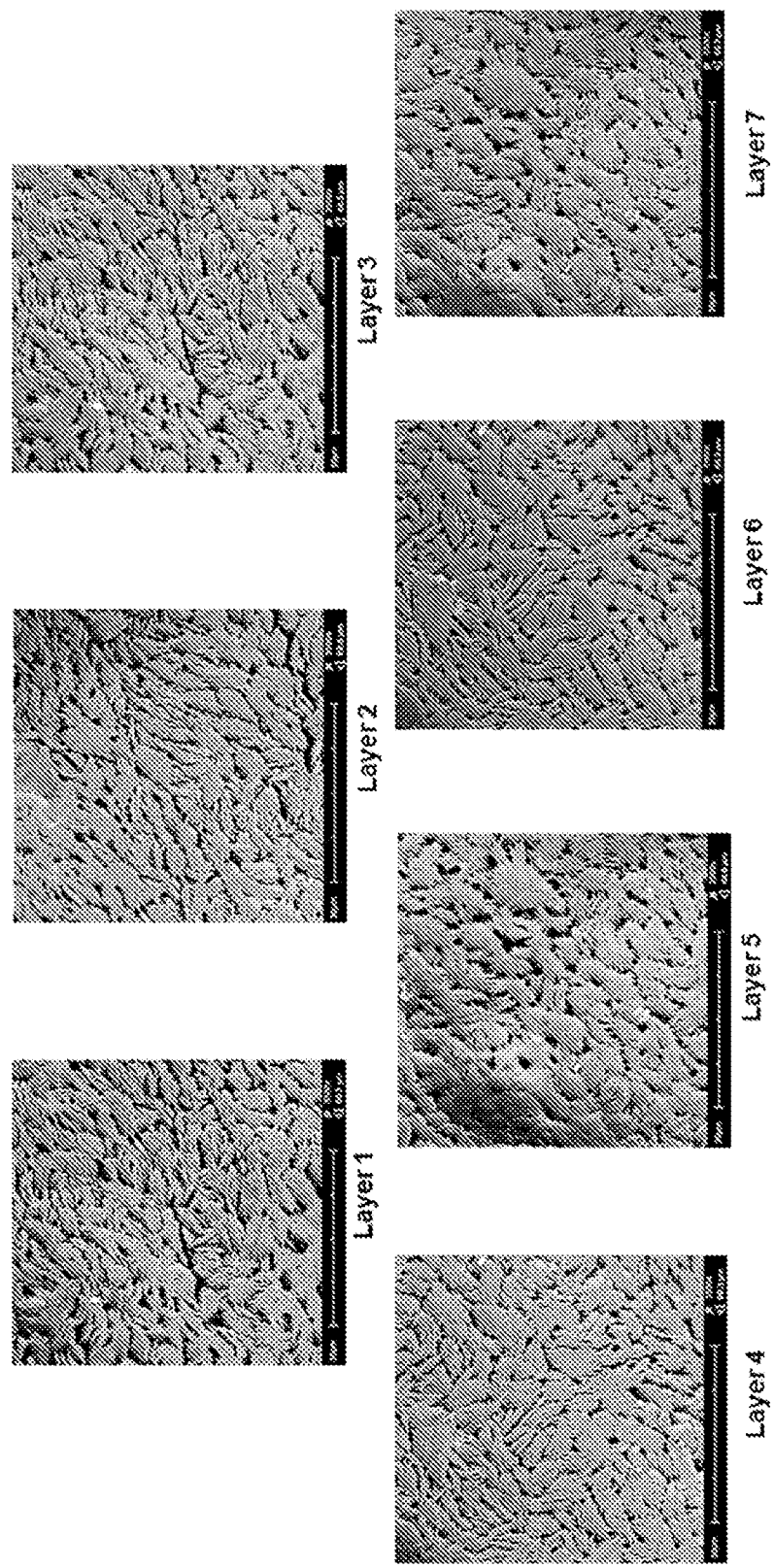
FIG. 18: shows a SEM analysis of the 3D bio-printed pseudo-bone scaffold at 3500 times magnification, demonstrating the micro-architecture and inner porous nature of the 7 layers of the designed 3D scaffold matrix.

Morphological Analysis Undertaken on the 3D Bioprinted Pseudo-Bone Scaffold:

Scanning electron microscopy was undertaken on the 3D bio-printed scaffold, determining the architectural design according to the programmed bio-printing parameters. This property was investigated and proved employing electron microscopy at an average 3500 times magnification. As seen in FIG. 18, each layer of the scaffold reflected similar porosity configuration, with uniformed intercalated threads of fibrous 3D printing, bioengineered for cell growth within the porous network. This configuration further allows easy diffusion of tissue medium through the scaffold matrix. Printing under low pressure and low speed parameters, thus allows for maximum consistency and uniformity in the micro-architectural design of the 3D scaffold. The intercalated "rope like" nature displayed in the micrograph, further emphasises the ability of the 3D scaffold to biodegrade gradually over time. Due to this highly porous condensed network architecture, the organization of the scaffold is also strengthened, due to the layers of bonding between each designed layer.

In Vitro Analysis of the Designed 3D Bioprinted Drug Delivery Scaffolds:

The 39 designed 3D scaffold formulations were analysed using sink conditions, with simvastatin release analysis. It was observed that as PPF polymer (8% $^w/_v$-20% $^w/_v$) was increased in percentage in the formulation, greater release of simvastatin loaded in the scaffold over 24 hours was observed. This can be attributed to the ester linkage of PPF, accounting for hydrolysis of the polymer into biocompatible and excretable degradation products of fumaric acid and propylene glycol [27].

Figure 19:
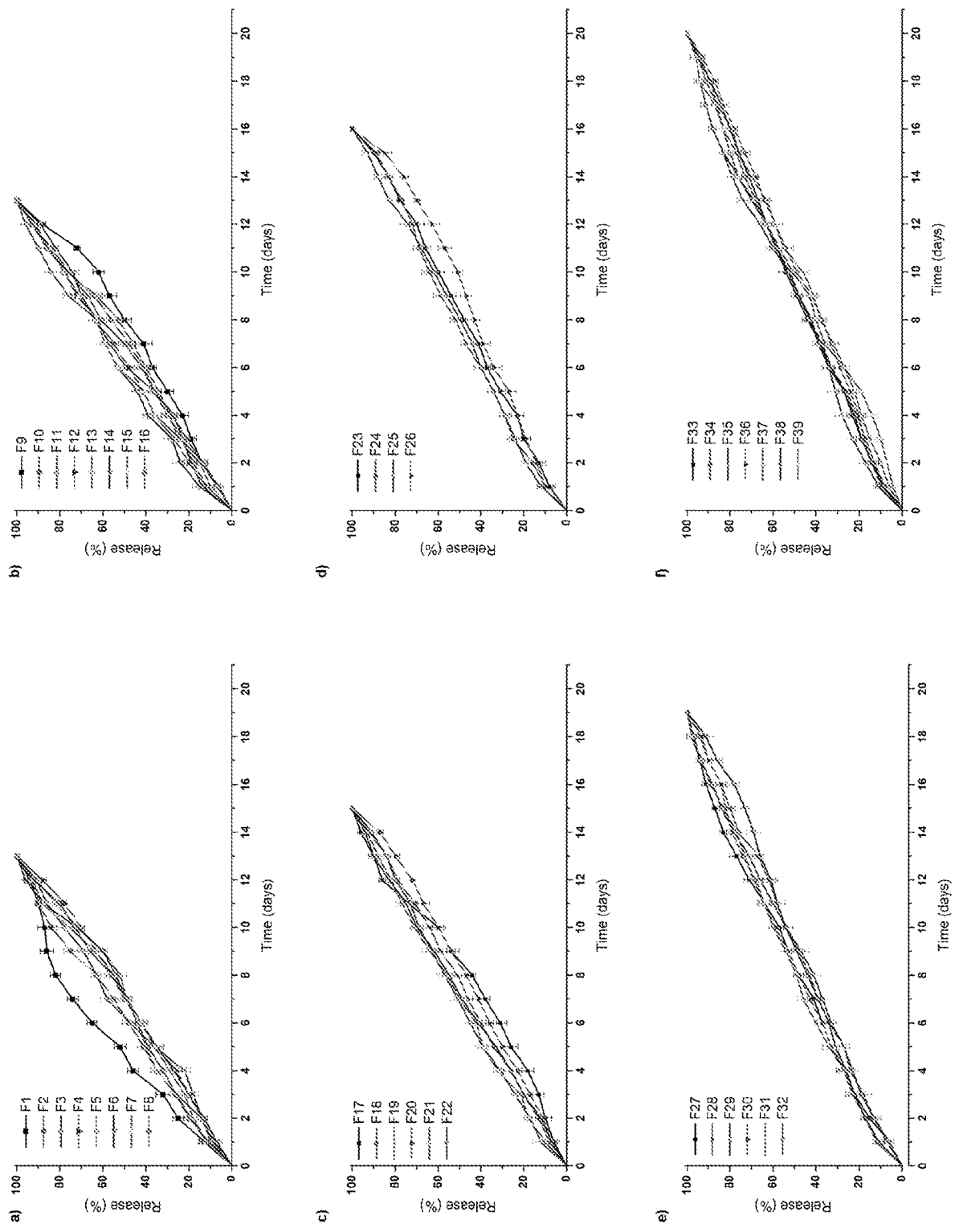
FIG. 19: In vitro simvastatin release analysis of the designed 3D bio-printed drug delivery scaffolds in (a) to (f).
Figure 20:
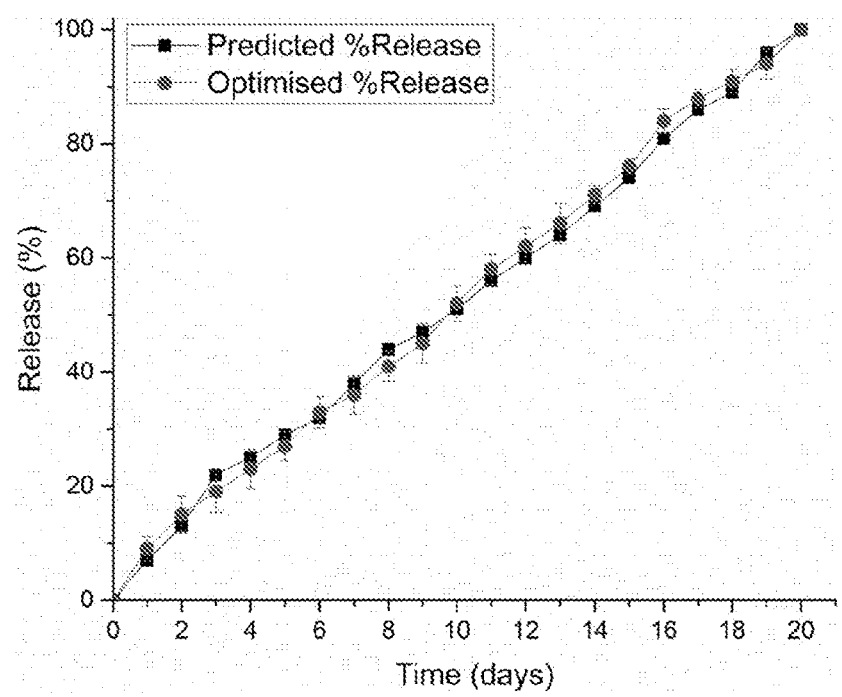
FIG. 20: shows an in vitro simvastatin release analysis of the optimized 3D bioprinted scaffold with predicted release kinetics using ANN modeling, both demonstrating drug release over 20-day duration.

PF127 was formulated as 14% $^w/_v$ to 16% $^w/_v$ formulations, increasing by 1% $^w/_v$ in variations to PPF. It was observed that, as the concentration of PF127 was present in the 3D scaffold, this gradually allowed slower release of the loaded drug from the formulation. This could possibly be explained in terms of increasing the amphiphilic nature of the 3D scaffold, resulting in greater controlled release profiles. Stimulus-responsive systems further produce physical and chemical changes when subjected to external signals, especially in thermo-responsive drug delivery systems, preventing particle aggregation, balancing hydrophilicity, surface roughness and surface charge [23]. As seen in FIG. 19, formulations 1-16 released up to 13 days, formulations 17-26 up to 16 days, formulations 27-32 up to 19 days and formulation 33-39 up to 20 days. The optimized 3D bio-printed scaffold formulation, resulting in the highest factor of response, was thus synthesised as 14% $^w/_v$ PPF and 16% $^w/_v$ PF127. Using this optimized formulation, the 3D bio-printed pseudo-bone scaffold was thus fabricated. The optimized 3D bio-printed scaffold displayed a controlled release of simvastatin over a 20-day duration, as seen in FIG. 20, with significant correlation to the predicted release kinetics undertaken using ANN. It can be further emphasized that the morphological configuration and details of specialised shape and internal architecture, significantly influenced the release kinetics and biodegradation of the 3D bio-printed drug delivery scaffold. It can be concluded that the optimized 3D bio-printed scaffold possessing highly specific design features of micro-architectural pores and uniformed bio-printed filaments of specific dimensional properties, has significant control release kinetics in vitro, with highly correlated release to the predicted ANN model.

Figure 21:
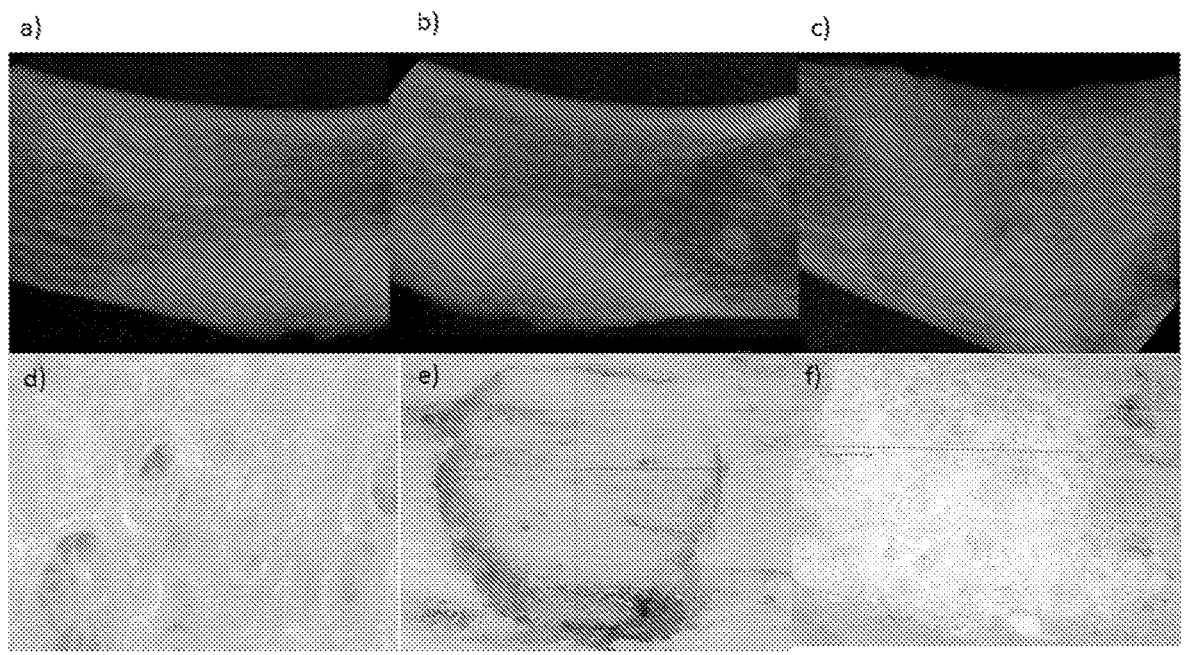
FIG. 21: shows a), b) and c) reflecting X-ray images of the human clavicle bone before fracture, after fracture and after treatment with the 3D bio-printed scaffold respectively. d) Light microscope image at 24 times magnification of the 3D bio-printed scaffold immersed in phosphate buffer solution, e) human clavicle bone induced with a fracture, representing missing bone fragments, f) human clavicle bone tested after incubation at 37.5° C. for 2 hours, demonstrating sealing of the induced fracture site, further analysed with properties of matrix hardness and resilience similar to original bone properties.

Matrix Analysis of the 3D Bioprinted Scaffold Evaluated Using Fracture Induced Human Clavicle Bones:

Mechanical properties of 3D scaffolds are essential, in relation to their site specific application [28, 29]. The MH and MR employing a texture analyser resulted in values of 18.61 N/mm and 9.48% respectively on the human clavicle before fracture. As seen in FIG. 21a, b and c; an X-ray image of the human clavicle bone before fracture, after fracture and after treatment with the 3D bio-printed scaffold respectively [29, 30]. After inducing the fracture and completion of in vitro analysis of the scaffold, it was found that a MH of 18.45 N/mm and MR of 9.33% was observed at the site of the fracture, which clearly represented missing bone mass, as seen in the X-ray image (FIG. 21b), as well as in FIG. 21e. FIG. 21d represents a light microscope image at 24 times magnification of the 3D bio-printed scaffold immersed in phosphate buffer solution. The light microscope, at low resolution (24× magnification) also proved significant filling of the fracture site, after incubation at 37.5° C. for 2 hours, as seen in FIG. 21f (the architecture of the bone and the scaffold sealed sites). These values of MH and MR further exemplifies the unique properties of the 3D bioprinted pseudo-bone scaffold to fill in fracture sites in bones, thus promoting greater adhesion of bone, and restoration of damaged bone to its intended mechanical integrity.

Conclusion:

A 3D bio-printed pseudo-bone drug delivery scaffold was designed to mimic the morphology, matrix strength and matrix resilience as healthy human bone. The 3D bio-printed scaffold was developed using computer aided design (CAD) software, with further optimization of the designed formulations, employing MATLAB® programing and artificial neural network. Polymers employed for formulating the 3D bio-printed scaffold, consisted of polypropylene fumarate (PPF), free radical polymerised polyethylene glycol-polycaprolactone (PEG-PCL-PEG) and Pluronic® (PF127). Simvastatin was incorporated in the 3D bio-printed scaffolds, designed to further increase bone healing and repair properties. The 3D bio-printed scaffold was characterized for its chemical, morphological, mechanical and in vitro release properties, evaluating its behaviour for application as an implantable scaffold at the site of fracture. The optimized 3D bio-printed scaffold, which resembled almost precise modeled release using ANN, demonstrated remarkable properties as a controlled release platform, which displayed biodegradation gradually over 20 days. The 3D bioprinted scaffold thus promoted contact adhesion between fractured/damaged bone using a human clavicle bone model, promoting the formation of a pseudo-bone matrix within the fractured site.

The Applicant believes that the PEG-PCL-PEG:PPF:PF127 thermoresponsive hydrogel according to this invention showcases properties that could not be expected upon an analysis of its component chemicals and/or component polymers. The properties include a 45 000 fold increase in strength upon attaining a predetermined temperature or temperature range. Further, SEM and TEM imaging shows the solid state three dimensional structure to mimic bone therein providing for not only a strong material at physiological conditions (akin to bone strength) but also a material having the solid and/or three dimensional characteristics of bone which will aid in healing processes associated with bone injury and/or defect.

The PEG-PCL-PEG:PPF:PF127 thermoresponsive hydrogel surprisingly provides a desired drug/API release profile lasting several days.

Further, the PEG-PCL-PEG:PPF:PF127 thermoresponsive hydrogel can also be formulated to provide an ink for a three dimensional printer allowing for a great diversity of uses.

The Applicant believes the invention is both novel and inventive.

REFERENCES

[1] Huang G, Wang L, Wang S, Han Y, Wu J, Zhang Q, Xu F and Lu T J 2012 Engineering three-dimensional cell mechanical microenvironment with hydrogels *Biofabrication* 4 042001
[2] Tang D, Tare R S, Yang L, Williams D F, Ou K and Oreffo R O C 2016 Biofabrication of bone tissue: approaches, challenges and translation for bone regeneration *Biomaterials* 83 363-382
[3] Caetano G, Violante R, Sant 'Ana A B, Murashima A B, Domingos M, Gibson A, Ba'rtolo P and Frade M A 2016 Cellularized versus decellularized scaffolds for bone regeneration *Materials Letters* 182 318-322
[4] Bosco A F, Faleiros P L, Carmona L R, Garcia V G, Theodoro L H, de Araujo N J, Nagata M J H and de Almeida J M 2016 Effects of low-level laser therapy on bone healing of critical-size defects treated with bovine bone graft. *Journal of Photochemistry and Photobiology B* 163 303-310
[5] Bose S, Vahabzadeh S and Bandyopadhyay A 2013 Bone tissue engineering using 3D printing *Materials Today* 16 (12) 496e504
[6] Mironov V, Trusk T, Kasyanov V, Little S, Swaja R and Markwald R 2009 Biofabrication: a 21st century manufacturing paradigm *Biofabrication* 1 022001
[7] Heintz K A, Bregenzer M E, Mantle J L, Lee K H, West J L and Slater J H 2016 Fabrication of 3D biomimetic microfluidic networks in hydrogels *Advanced Healthcare Materials* 5 (17) 2153e2160
[8] Li J, He L, Zhou C, Zhou Y, Bai Y and Lee F Y 2015 3D printing for regenerative medicine: from bench to bedside, *MRS Bulletin* (3D printing of biomaterials) 40 145e154
[9] Lee J S, Hong J M, Jung J W, Shim J H, Oh J H and Cho D W 2014 3D printing of composite tissue with complex shape applied to ear regeneration *Biofabrication* 6 024103
[10] Huang G, Wang L, Wang S, Han Y, Wu J, Zhang Q, Xu F and Lu T J 2012 Engineering three-dimensional cell mechanical microenvironment with hydrogels *Biofabrication* 4 042001
[11] Chua C K and Leong K F 2014 3D Printing and Additive Manufacturing: Principles and Applications of Rapid Prototyping, fourth ed. World Scientific, Singapore
[12] Gioffredi E, Boffito M, Calzone S, Giannitelli S M, Rainer A, Trombetta M, Mozetic P and Chiono V 2016 Pluronic® F127 hydrogel characterization and biofabrication in cellularized constructs for tissue engineering applications. *Procedia CIRP* 49 125-132
[13] Kang K H, Hockaday L A and Butcher J T 2013 Quantitative optimization of solid freeform deposition of aqueous hydrogels *Biofabrication* 5 035001
[14] Wang C, Tang Z, Zhao Y, Yao R, LiL and Sun W 2014 Three-dimensional in vitro cancer models: a short review *Biofabrication* 6 022001
[15] Arai K, Iwanaga S, Toda H, Genci C, Nishiyama Y and Nakamura M 2011 Three-dimensional inkjet biofabrication based on designed images *Biofabrication* 3 034113
[16] Choonara Y E, du Toit L C, Kumar P, Kondiah P P D and Pillay V 2016 3D-printing and the effect on medical costs: A new era? *Expert Review of Pharmacoeconomics & Outcomes Research* 16(1) 23-32
[17] Faulkner-Jones A, Fyfe C, Cornelissen D J, Gardner J, King J, Courtney A and Shu W 2015 Bioprinting of human pluripotent stem cells and their directed differentiation into hepatocyte-like cells for the generation of mini-livers in 3D *Biofabrication* 7 044102
[18] Shim J H, Kim J Y, Park M, Park J and Cho D W 2011 Development of a hybrid scaffold with synthetic biomaterials and hydrogel using solid freeform fabrication technology *Biofabrication* 3 034102
[19] Kondiah P J, Choonara Y E, Kondiah P P D, Kumar P, Marimuthu T, du Toit L C and Pillay V 2017 Development of an injectable pseudo-bone thermo-gel for application in small bone fractures *International Journal of Pharmaceutics* 520 39-48
[20] Agami N, Atiya A, Saleh M and El-Shishiny H 2009 A neural network based dynamic forecasting model for trend impact analysis *Technological Forecasting and Social Change* 76 952-962
[21] Zhang W, Shi Y, Chen Y, Ye J, Sha X and Fang X 2011 Multifunctional Pluronic® P123/F127 mixed polymeric micelles loaded with paclitaxel for the treatment of multidrug resistant tumors *Biomaterials* 32 2894-2906
[22] Sanchez-Molina D, Velazquez-Ameijide J, Quintana V, Arregui-Dalmasesa C, Crandall J R, Subit D and Kerrigan J R 2013. Fractal dimension and mechanical properties of human cortical bone *Medical Engineering & Physics* 35 576-582
[23] Raval A, Pillai S A, Bahadur A and Bahadur P 2017 Systematic characterization of Pluronic® micelles and their application for solubilization and in vitro release of some hydrophobic anticancer drugs *Journal of Molecular Liquids* 230 473-481

[24] Zhou Q, Zhang Z, Chen T, Guo X and Zhou S 2011 Preparation and characterization of thermosensitive Pluronic® F127-b-poly(e-caprolactone) mixed micelles. *Colloids and Surfaces B: Biointerfaces* 86 45-57

[25] Behravesh E, Shung A K, Jo S and Mikos A G 2002 Synthesis and characterization of triblock copolymers of methoxy poly(ethylene glycol) and poly(propylene fumarate). *Biomacromolecules* 3 153-158

[26] Jo S, Engel P S and Mikos A G 2000 Synthesis of poly(ethylene glycol)-tethered poly (propylene fumarate) and its modification with GRGD peptide *Polymer* 41 7595-7604

[27] Salarian M, Xu W M, Biesingerc M C and Charpentier P A 2014 Synthesis and characterization of novel TiO2-poly(propylene fumarate) nanocomposites for bone cementation *Journal of Materials Chemistry B* 2 5145-5156

[28] Hockaday L A et al 2012 Rapid 3D printing of anatomically accurate and mechanically heterogeneous aortic valve hydrogel scaffolds *Biofabrication* 4 035005

[29] Xu T, Binder K W, Albanna M Z, Dice D, Zhao W, Yoo J J and Atala A 2013 Hybrid printing of mechanically and biologically improved constructs for cartilage tissue engineering applications *Biofabrication* 5 015001

[30] Iannolo M, Werner F W, Sutton L G, Serell S M and VanValkenburg S M 2010 Forces across the middle of the intact clavicle during shoulder motion *Journal of Shoulder and Elbow Surgery* 19 1013-1017

The invention claimed is:

1. A thermoresponsive hydrogel comprising a polyethylene glycol-polycaprolactone-polyethylene glycol (PEG-PCL-PEG) copolymer, polypropylene fumarate (PPF), and a poloxamer (POL), wherein the PEG-PCL-PEG:PPF:POL thermoresponsive hydrogel is reversibly thermoresponsive across a temperature range transitioning from a sol state, at about 20° C. or below about 20° C., to a gel state, at about 36.5° C. or above 36.5° C.

2. The thermoresponsive hydrogel according to claim 1, wherein the poloxamer is poloxamer 407, therein providing a PEG-PCL-PEG:PPF:poloxamer 407 thermoresponsive hydrogel.

3. The thermoresponsive hydrogel according to claim 2, further comprising an active pharmaceutical ingredient (API) dispersed therein.

4. The thermoresponsive hydrogel according to claim 3, wherein the active pharmaceutical ingredient (API) is an API falling in the Biopharmaceutics Classification System (BCS) class II.

5. The thermoresponsive hydrogel according to claim 4, wherein the API of BCS class II comprises statins.

6. A method of manufacturing the thermoresponsive hydrogel according to claim 1, the method comprising the following steps:
   (i). mixing ε-caprolactone (CL) and polyethylene glycol (PEG) together under inert conditions in the presence of a catalyst to form, via free radical polymerization, a first reaction mixture including a polyethylene glycol-polycaprolactone-polyethylene glycol (PEG-PCL-PEG) copolymer;
   (ii). adding polypropylene fumarate (PPF) to the first reaction mixture forming a second reaction mixture; and
   (iii). mixing a poloxamer (POL) into the second reaction mixture to form a third reaction mixture including the thermoresponsive hydrogel according to claim 1.

7. The method according to claim 6, wherein the poloxamer is poloxamer 407.

8. The method according to claim 7, wherein the catalyst is stannous octoate ($Sn(Oct)_2$).

9. The method according to claim 8, wherein mixing of step (i) takes place at about 125° C. for between about 4 and 8 hours, and wherein step (ii) takes place at about 140° C. for between 4 and 8 hours.

10. The thermoresponsive hydrogel according to claim 1 for use in the treatment of bone injury and/or bone defects.

11. The thermoresponsive hydrogel for use according to claim 10, wherein the thermoresponsive hydrogel is for administration by injection in the sol state at a site of bone injury and/or bone defect in a human or animal body, and wherein said injected thermoresponsive hydrogel transitions to a gel state at said site.

12. An ink for a three dimensional printing device, the ink comprising the thermoresponsive hydrogel according to claim 1.

\* \* \* \* \*